United States Patent [19]

Harris et al.

[11] Patent Number: 5,472,856
[45] Date of Patent: Dec. 5, 1995

[54] RECOMBINANT HUMAN THYMOPOIETIN PROTEINS AND USES THEREFOR

[75] Inventors: Crafford A. Harris, Easton, Pa.; Gideon Goldstein, Short Hills, N.J.; John J. Siekierka, Towaco, N.J.; Mary A. Talle, Piscataway, N.J.; Ponniah Shenbagamurthi, Bridgewater, N.J.; Michael D. Culler, Easton, Pa.; Diane R. Setcavage, Milford, N.J.

[73] Assignee: Immunobiology Research Institute, Inc., Annandale, N.J.

[21] Appl. No.: 171,382

[22] Filed: Dec. 21, 1993

[51] Int. Cl.$^6$ .......................... C12N 15/09; C12N 15/63; C12P 21/02
[52] U.S. Cl. .................. 435/69.1; 435/240.2; 435/252.3; 435/252.3; 435/254.11; 435/320.1; 435/252.33; 536/23.1
[58] Field of Search ................................ 435/69.1, 240.2, 435/240.1, 320.1, 252.3, 254.11, 252.33; 536/23.1; 530/350

[56] References Cited

U.S. PATENT DOCUMENTS

| | | | |
|---|---|---|---|
| 4,002,740 | 1/1977 | Goldstein et al. | 424/177 |
| 4,077,949 | 3/1978 | Goldstein | 260/112.5 |
| 4,120,951 | 10/1978 | Goldstein | 424/177 |
| 4,190,646 | 2/1980 | Goldstein et al. | 424/177 |
| 4,745,051 | 5/1988 | Smith et al. | 435/68 |
| 4,923,964 | 5/1990 | Goldstein et al. | 530/324 |

FOREIGN PATENT DOCUMENTS 502607  9/1992  European Pat. Off. .

OTHER PUBLICATIONS

Sambrook et al. Molecular Cloning, A Lab. Manual, vol. 3, chip 16, pp. 16.2–16.31 Cold Spring Harbor Lab. Press, 1989.
C. Harris et al, "Three Distinct Human Thymopoietins are Derived from Alternatively Spliced mRNAs", *Proc. Natl. Acad. Sci. USA*, 91(14):6283–6287 (Jul. 1994).
C. Harris et al, "Multiple Distinct Human Thymopoietins are Derived from Alternatively Spliced mRNAs", *Mol. Biol. of the Cell*, 4(Suppl.):453a, Abstract No. 2632 (Oct. 1993).
K. Bolla et al, "Prevention of Recurrences in Frequently Relapsing Herpes Labialis with Thymopentin", *Surv. Immunol. Res.*, 4(1):37–47 (1985).
E. Sundal and K. Bolla, "Therapy with Thymopentin: A Clinical Overview", *Immune Regulation by Characterized Polypeptides*, ed. Alan R. Liss, Inc., pp. 121–136 (1987).
G. Goldstein et al, "Isolation of Bovine Thymin: A Polypeptide Hormone of the Thymus", *Nature*, 247(5435):11–14 (Jan. 4, 1974) [Goldstein I].
G. Goldstein et al, "A Synthetic Pentapeptide with Biological Activity Characteristic of the Thymic Hormone Thymopoietin", *Science*, 204:1309–1310 (Jun. 22, 1979).
M. Scheid et al, "The Generation and Regulation of Lymphocyte Populations, Evidence from Differentiative Induction Systems in vitro", *J. Exp. Med.*, 147:1727–1743 (Jun. 1, 1978) [Scheid I].
M. Scheid et al, "Differentiation of T Cells in Nude Mice", *Science*, 190:1211–1213 (Dec. 19, 1975) [Scheid II].
K. Venkatasubramanian et al, "Binding of Thymopoietin to the Acetylcholine Receptor", *Proc. Natl. Acad. Sci. USA*, 83:3171–3174 (May 1986).
T. Abiko et al, "Syntheses and Effects of a Thymopoietin II Fragment and its Analogs on the Impaired T–Cell Transformation in a Patient with Common Variable Immunodeficiency", *J. Appl. Biochem.*, 7:408–422 (publ. Dec. 1985; mailing date Mar. 11, 1986).
D. Schlesinger et al, "The Amino Acid Sequence of Thymopoietin II", *Cell*, 5:361–365 (Aug. 1975).
T. Audhya et al, "Complete Amino Acid Sequences of Bovine Thymopoietins I, II, and III: Closely Homologous Polypeptides", *Biochemistry*, 20(21):6195–6200 (Oct. 16, 1981).
D. Zevin–Sonkin et al, "Molecular Cloning of the Bovine Thymopoietin Gene and its Expression in Different Calf Tissues: Evidence for a Predominant Expression in Thymocytes", *Immunol. Lett.*, 31:301–310 (Jan. 12, 1992).
R. Basch et al, "Induction of T–Cell Differentiation in Vitro by Thymin, a Purified Polypeptide Hormone of the Thymus", *Proc. Natl. Acad. Sci. USA*, 71(4):1474–1478 (Apr. 1974) [Basch I].
D. Schlesinger et al, "Chemical Synthesis of a Peptide Fragment of Thymopoietin II that Induces Selective T Cell Differentiation", *Cell*, 5:367–370 (Aug. 1975) [Schlesinger II].
R. A. Basch et al, "Thymopoietin–Induced Acquisition of Responsiveness to T Cell Mitogens", *Cell. Immunol.*, 20:218–228 (publ. Dec. 1975; mailing date Jan. 7, 1976) [Basch II].
G. Goldstein et al, "Thymopoietin and Myasthenia Gravis: Neostigmine–Responsive Neuromuscular Block Produced in Mice by a Synthetic Peptide Fragment of Thymopoietin", *Lancet*, 2:256–262 (Aug. 9, 1975) [Goldstein III].
G. Sunshine et al, "Thymopoietin Enhances the Allogeneic Response and Cyclic GMP Levels of Mouse Peripheral, Thymus–Derived Lymphocytes", *J. Immunol.*, 120(5):1594–1599 (May 1978).
R. Brown et al, "Immunoreactive Thymopoietin in the Mouse Central Nervous System", *Brain Research*, 381:237–243 (Aug. 6, 1986).
T. Audhya et al, "Contrasting Biological Activities of Thymopoietin and Splenin, Two Closely Related Polypeptide Products of Thymus and Spleen", *Proc. Natl. Acad. Sci. USA*, 81:2847–2849 (May 1984) [Audhya II].
T. Audhya et al, "Isolation and Complete Amino Acid Sequence of Human Thymopoietin and Splenin", *Proc. Natl. Acad. Sci. USA*, 84:3545–3549 (Jun. 1987) [Audhya III].

(List continued on next page.)

Primary Examiner—Stephen G. Walsh
Assistant Examiner—Sally P. Teng
Attorney, Agent, or Firm—Howson and Howson

[57] ABSTRACT

The present invention provides novel nucleotide and amino acid sequences for human thymopoietin α, β, and γ, methods of recombinantly expressing same, and diagnostic and therapeutic uses thereof.

13 Claims, 11 Drawing Sheets

OTHER PUBLICATIONS

G. Goldstein, "Lymphocyte Differentiations Induced by Thymopoietin, Bursopoietin and Ubiquitin", Molecular Control of Proliferation and Differentiation, Academic Press, Inc., pp. 197–202 (Feb. 1978) [Goldstein IV].

G. Goldstein et al, "Thymopoietin and Bursopoietin: Induction Signals Regulating Early Lymphocyte Differentiation", Cold Spring Harbor Symposia on Quantitative Biology, vol. XLI, pp. 5–8, Cold Spring Harbor Laboratory (1977) [Goldstein V].

M. Quik et al, "Evidence for Thymopoietin and Thymopoietin/alpha–bungarotoxin/nicotinic Receptors within the Brain", Proc. Natl. Acad. Sci. USA, 88:2603–2607 (Mar. 1991) [Quik I].

M. Quik et al, "Thymopoietin Inhibits Function and Ligand Binding to Nicotinic Receptors at the Neuromuscular Junction", J. Pharm. Exp. Therm., 254(3):1113–1119 (Jul. 1990) [Quik II].

M. Quik et al, "Rapid Communication—Thymopoietin, a Thymic Polypeptide, Specifically Interacts at Neuronal Nicotinic alpha–Bungarotoxin Receptors", J. Neurochemistry, 53(4):1320–1323 (Sep. 12, 1989) [Quik III].

F. Revah et al, "Calcium–Dependent Effect of the Thymic Polypeptide Thymopoietin on the Desensitization of the Nicotinic Acetylcholine Receptor", Proc. Natl. Acad. Sci. USA, 84:3477–3481 (May 1987).

FIGURE 1A

DNA and Amino Acid Sequences of TP α

GTTCGTAGTT CGGCTCTGGG GTCTTTTGTG TCCGGGTCTG GCTTGGCTTT GTGTCCGCGA

GTTTTTGTTC CGCTCCGCAG CGCTCTTCCC GGGCAGGAGC CGTGAGGCTC GGAGGCGGCA

GCGCGGTCCC CGGCCAGGAG CAAGCGCGCC GGCGTGAGCG GCGGCGGCAA AGGCTGTGGG

```
                                           -1  +1
GAGGGGCTT CGCAGATCCC CGAG ATG  CCG GAG TTC CTG GAA GAC CCC TCG
                          Met  Pro Glu Phe Leu Glu Asp Pro Ser
                          -1   +1                  5

GTC CTG ACA AAA GAC AAG TTG AAG AGT GAG TTG GTC GCC AAC AAT GTG
Val Leu Thr Lys Asp Lys Leu Lys Ser Glu Leu Val Ala Asn Asn Val
    10              15                  20

ACG CTG CCG GCC GGG GAG CAG CGC AAA GAC GTG TAC GTC CAG CTC TAC
Thr Leu Pro Ala Gly Glu Gln Arg Lys Asp Val Tyr Val Gln Leu Tyr
25              30                  35                      40

CTG CAG CAC CTC ACG GCT CGC AAC CGG CCG CCG CTC CCC GCC GGC ACC
Leu Gln His Leu Thr Ala Arg Asn Arg Pro Pro Leu Pro Ala Gly Thr
            45                  50                  55

AAC AGC AAG GGG CCC CCG GAC TTC TCC AGT GAC GAA GAG CGC GAG CCC
Asn Ser Lys Gly Pro Pro Asp Phe Ser Ser Asp Glu Glu Arg Glu Pro
            60                  65                  70

ACC CCG GTC CTC GGC TCT GGG GCC GCC GCC GCG GGC CGG AGC CGA GCA
Thr Pro Val Leu Gly Ser Gly Ala Ala Ala Ala Gly Arg Ser Arg Ala
        75                  80                  85

GCC GTC GGC AGG AAA GCC ACA AAA AAA ACT GAT AAA CCC AGA CAA GAA
Ala Val Gly Arg Lys Ala Thr Lys Lys Thr Asp Lys Pro Arg Gln Glu
    90                  95                  100

GAT AAA GAT GAT CTA GAT GTA ACA GAG CTC ACT AAT GAA GAT CTT TTG
Asp Lys Asp Asp Leu Asp Val Thr Glu Leu Thr Asn Glu Asp Leu Leu
105             110                 115                     120

GAT CAG CTT GTG AAA TAC GGA GTG AAT CCT GGT CCT ATT GTG GGA ACA
Asp Gln Leu Val Lys Tyr Gly Val Asn Pro Gly Pro Ile Val Gly Thr
                125                 130                     135

ACC AGG AAG CTA TAT GAG AAA AAG CTT TTG AAA CTG AGG GAA CAA GGA
Thr Arg Lys Leu Tyr Glu Lys Lys Leu Leu Lys Leu Arg Glu Gln Gly
            140                 145                 150
```

FIGURE 1B

| ACA | GAA | TCA | AGA | TCT | TCT | ACT | CCT | CTG | CCA | ACA | ATT | TCT | TCT | TCA | GCA |
|---|---|---|---|---|---|---|---|---|---|---|---|---|---|---|---|
| Thr | Glu | Ser | Arg | Ser | Ser | Thr | Pro | Leu | Pro | Thr | Ile | Ser | Ser | Ser | Ala |
|  |  | 155 |  |  |  |  | 160 |  |  |  |  | 165 |  |  |  |

| GAA | AAT | ACA | AGG | CAG | AAT | GGA | AGT | AAT | GAT | TCT | GAC | AGA | TAC | AGT | GAC |
|---|---|---|---|---|---|---|---|---|---|---|---|---|---|---|---|
| Glu | Asn | Thr | Arg | Gln | Asn | Gly | Ser | Asn | Asp | Ser | Asp | Arg | Tyr | Ser | Asp |
|  | 170 |  |  |  | 175 |  |  |  |  | 180 |  |  |  |  |  |

| AAT | GAA | GAA | GGA | AAG | AAG | AAA | GAA | CAC | AAG | AAA | GTG | AAG | TCC | ACT | AGG |
|---|---|---|---|---|---|---|---|---|---|---|---|---|---|---|---|
| Asn | Glu | Glu | Gly | Lys | Lys | Lys | Glu | His | Lys | Lys | Val | Lys | Ser | Thr | Arg |
| 185 | * |  |  | 190 |  |  |  |  |  |  | 195 |  |  |  | 200 |

| GAT | ATT | GTT | CCT | TTT | TCT | GAA | CTT | GGA | ACT | ACT | CCC | TCT | GGT | GGT | GGA |
|---|---|---|---|---|---|---|---|---|---|---|---|---|---|---|---|
| Asp | Ile | Val | Pro | Phe | Ser | Glu | Leu | Gly | Thr | Thr | Pro | Ser | Gly | Gly | Gly |
|  |  |  |  | 205 |  |  |  |  | 210 |  |  |  |  | 215 |  |

| TTT | TTT | CAG | GGT | ATT | TCT | TTT | CCT | GAA | ATC | TCC | ACC | CGT | CCT | CCT | TTG |
|---|---|---|---|---|---|---|---|---|---|---|---|---|---|---|---|
| Phe | Phe | Gln | Gly | Ile | Ser | Phe | Pro | Glu | Ile | Ser | Thr | Arg | Pro | Pro | Leu |
|  |  |  | 220 |  |  |  |  | 225 |  |  |  |  | 230 |  |  |

| GGC | AGT | ACC | GAA | CTA | CAG | GCA | GCT | AAG | AAA | GTA | CAT | ACT | TCT | AAG | GGA |
|---|---|---|---|---|---|---|---|---|---|---|---|---|---|---|---|
| Gly | Ser | Thr | Glu | Leu | Gln | Ala | Ala | Lys | Lys | Val | His | Thr | Ser | Lys | Gly |
|  |  | 235 |  |  |  |  | 240 |  |  |  |  | 245 |  |  |  |

| GAC | CTA | CCT | AGG | GAG | CCT | CTT | GTT | GCC | ACA | AAC | TTG | CCT | GGC | AGG | GGA |
|---|---|---|---|---|---|---|---|---|---|---|---|---|---|---|---|
| Asp | Leu | Pro | Arg | Glu | Pro | Leu | Val | Ala | Thr | Asn | Leu | Pro | Gly | Arg | Gly |
|  | 250 |  |  |  |  | 255 |  |  |  |  |  | 260 |  |  |  |

| CAG | TTG | CAG | AAG | TTA | GCC | TCT | GAA | AGG | AAT | TTG | TTT | ATT | TCA | TGC | AAG |
|---|---|---|---|---|---|---|---|---|---|---|---|---|---|---|---|
| Gln | Leu | Gln | Lys | Leu | Ala | Ser | Glu | Arg | Asn | Leu | Phe | Ile | Ser | Cys | Lys |
| 265 |  |  |  |  | 270 |  |  |  |  | 275 |  |  |  |  | 280 |

| TCT | AGC | CAT | GAT | AGG | TGT | TTA | GAG | AAA | AGT | TCT | TCG | TCA | TCT | TCT | CAG |
|---|---|---|---|---|---|---|---|---|---|---|---|---|---|---|---|
| Ser | Ser | His | Asp | Arg | Cys | Leu | Glu | Lys | Ser | Ser | Ser | Ser | Ser | Ser | Gln |
|  |  |  | 285 |  |  |  |  |  | 290 |  |  |  |  | 295 |  |

| CCT | GAA | CAC | AGT | GCC | ATG | TTG | GTC | TCT | ACT | GCA | GCT | TCT | CCT | TCA | CTG |
|---|---|---|---|---|---|---|---|---|---|---|---|---|---|---|---|
| Pro | Glu | His | Ser | Ala | Met | Leu | Val | Ser | Thr | Ala | Ala | Ser | Pro | Ser | Leu |
|  |  |  | 300 |  |  |  |  | 305 |  |  |  |  | 310 |  |  |

| ATT | AAA | GAA | ACC | ACC | ACT | GGT | TAC | TAT | AAA | GAC | ATA | GTA | GAA | AAT | ATT |
|---|---|---|---|---|---|---|---|---|---|---|---|---|---|---|---|
| Ile | Lys | Glu | Thr | Thr | Thr | Gly | Tyr | Tyr | Lys | Asp | Ile | Val | Glu | Asn | Ile |
|  |  | 315 |  |  |  |  | 320 |  |  |  |  | 325 |  |  |  |

| TGC | GGT | AGA | GAG | AAA | AGT | GGA | ATT | CAA | CCA | TTA | TGT | CCT | GAG | AGG | TCC |
|---|---|---|---|---|---|---|---|---|---|---|---|---|---|---|---|
| Cys | Gly | Arg | Glu | Lys | Ser | Gly | Ile | Gln | Pro | Leu | Cys | Pro | Glu | Arg | Ser |
|  | 330 |  |  |  | 335 |  |  |  |  | 340 |  |  |  |  |  |

| CAT | ATT | TCA | GAT | CAA | TCG | CCT | CTC | TCC | AGT | AAA | AGG | AAA | GCA | CTA | GAA |
|---|---|---|---|---|---|---|---|---|---|---|---|---|---|---|---|
| His | Ile | Ser | Asp | Gln | Ser | Pro | Leu | Ser | Ser | Lys | Arg | Lys | Ala | Leu | Glu |
| 345 |  |  |  | 350 |  |  |  |  |  | 355 |  |  |  |  | 360 |

FIGURE 1C

| | | | | | | | | | | | | | | |
|---|---|---|---|---|---|---|---|---|---|---|---|---|---|---|
| GAG | TCT | GAG | AGC | TCA | CAA | CTA | ATT | TCT | CCG | CCA | CTT | GCC | CAG | GCA | ATC |
| Glu | Ser | Glu | Ser | Ser | Gln | Leu | Ile | Ser | Pro | Pro | Leu | Ala | Gln | Ala | Ile |
| | | | | 365 | | | | | 370 | | | | | 375 | |

```
GAG TCT GAG AGC TCA CAA CTA ATT TCT CCG CCA CTT GCC CAG GCA ATC
Glu Ser Glu Ser Ser Gln Leu Ile Ser Pro Pro Leu Ala Gln Ala Ile
            365             370             375

AGA GAT TAT GTC AAT TCT CTG TTG GTC CAG GGT GGG GTA GGT AGT TTG
Arg Asp Tyr Val Asn Ser Leu Leu Val Gln Gly Gly Val Gly Ser Leu
            380             385             390

CCT GGA ACT TCT AAC TCT ATG CCC CCA CTG GAT GTA GAA AAC ATA CAG
Pro Gly Thr Ser Asn Ser Met Pro Pro Leu Asp Val Glu Asn Ile Gln
            395             400             405

AAG AGA ATT GAT CAG TCT AAG TTT CAA GAA ACT GAA TTC CTG TCT CCT
Lys Arg Ile Asp Gln Ser Lys Phe Gln Glu Thr Glu Phe Leu Ser Pro
            410             415             420

CCA AGA AAA GTC CCT AGA CTG AGT GAG AAG TCA GTG GAG GAA AGG GAT
Pro Arg Lys Val Pro Arg Leu Ser Glu Lys Ser Val Glu Glu Arg Asp
425             430             435             440

TCA GGT TCC TTT GTG GCA TTT CAG AAC ATA CCT GGA TCC GAA CTG ATG
Ser Gly Ser Phe Val Ala Phe Gln Asn Ile Pro Gly Ser Glu Leu Met
            445             450             455

TCT TCT TTT GCC AAA ACT GTT GTC TCT CAT TCA CTC ACT ACC TTA GGT
Ser Ser Phe Ala Lys Thr Val Val Ser His Ser Leu Thr Thr Leu Gly
            460             465             470

CTA GAA GTG GCT AAG CAA TCA CAG CAT GAT AAA ATA GAT GCC TCA GAA
Leu Glu Val Ala Lys Gln Ser Gln His Asp Lys Ile Asp Ala Ser Glu
            475             480             485

CTA TCT TTT CCC TTC CAT GAA TCT ATT TTA AAA GTA ATT GAA GAA GAA
Leu Ser Phe Pro Phe His Glu Ser Ile Leu Lys Val Ile Glu Glu Glu
            490             495             500

TGG CAG CAA GTT GAC AGG CAG CTG CCT TCA CTG GCA TGC AAA TAT CCA
Trp Gln Gln Val Asp Arg Gln Leu Pro Ser Leu Ala Cys Lys Tyr Pro
505             510             515             520

GTT TCT TCC AGG GAG GCA ACA CAG ATA TTA TCA GTT CCA AAA GTA GAT
Val Ser Ser Arg Glu Ala Thr Gln Ile Leu Ser Val Pro Lys Val Asp
            525             530             535

GAT GAA ATC CTA GGG TTT ATT TCT GAA GCC ACT CCA CTA GGA GGT ATT
Asp Glu Ile Leu Gly Phe Ile Ser Glu Ala Thr Pro Leu Gly Gly Ile
            540             545             550

CAA GCA GCC TCC ACT GAG TCT TGC AAT CAG CAG TTG GAC TTA GCA CTC
Gln Ala Ala Ser Thr Glu Ser Cys Asn Gln Gln Leu Asp Leu Ala Leu
            555             560             565
```

FIGURE 1D

```
TGT AGA GCA TAT GAA GCT GCA GCA TCA GCA TTG CAG ATT GCA ACT CAC
Cys Arg Ala Tyr Glu Ala Ala Ala Ser Ala Leu Gln Ile Ala Thr His
    570             575                 580

G
ACT GCC TTT GTA GCT AAG GCT ATG CAG GCA GAC ATT AGT CAA GCT GCA
Thr Ala Phe Val Ala Lys Ala Met Gln Ala Asp Ile Ser Gln Ala Ala
585             590                 595         Glu      600

CAG ATT CTT AGC TCA GAT CCT AGT CGT ACC CAC CAA GCG CTT GGG ATT
Gln Ile Leu Ser Ser Asp Pro Ser Arg Thr His Gln Ala Leu Gly Ile
                605                 610                 615

CTG AGC AAA ACA TAT GAT GCA GCC TCA TAT ATT TGT GAA GCT GCA TTT
Leu Ser Lys Thr Tyr Asp Ala Ala Ser Tyr Ile Cys Glu Ala Ala Phe
         620                 625                 630

GAT GAA GTG AAG ATG GCT GCC CAT ACC ATG GGA AAT GCC ACT GTA GGT
Asp Glu Val Lys Met Ala Ala His Thr Met Gly Asn Ala Thr Val Gly
         635                 640                 645

CGT CGA TAC CTC TGG CTG AAG GAT TGC AAA ATT AAT TTA GCT TCT AAG
Arg Arg Tyr Leu Trp Leu Lys Asp Cys Lys Ile Asn Leu Ala Ser Lys
    650                 655                 660

AAT AAG CTG GCT TCC ACT CCC TTT AAA GGT GGA ACA TTA TTT GGA GGA
Asn Lys Leu Ala Ser Thr Pro Phe Lys Gly Gly Thr Leu Phe Gly Gly
665             670                 675                 680

GAA GTA TGC AAA GTA ATT AAA AAG CGT GGA AAT AAA CAC TAGTAAAATT
Glu Val Cys Lys Val Ile Lys Lys Arg Gly Asn Lys His
                685                 690
```

AAGGACAAAA AGACATCTAT CTTATCTTTC AGGTACTTTA TGCCAACATT TTCTTTTCTG

TTAAGGTTGT TTTAGTTTCC AGATAGGGCT AATTACAAAA TGTTAAGCTT CTACCCATCA

AATTACAGTA TAAAAGTAAT TGCCTGTGTA GAACTACTTG TCTTTTCTAA AGATTTGCGT

AGATAGGAAG CCTG

FIGURE 2A

DNA and Amino Acid Sequence of TP β

GGTTGGTGCG AGCTTCCAGC TTGGCCGCAG TTGGTTCGTA GTTCGGCTCT GGGGTCTTTT

GTGTCCGGGT CTGGCTTGGC TTTGTGTCCG CGAGTTTTTG TTCCGCTCCG CAGCGCTCTT

CCCGGGCAGG AGCCGTGAGG CTCGGAGGCG GCAGCGCGGT CCCCGGCCAG GAGCAAGCGC

GCCGGCGTGA GCGGCGGCGG CAAAGGCTGT GGGGAGGGGG CTTCGCAGAT CCCCGAG

```
-1 +1
ATG  CCG GAG TTC CTG GAA GAC CCC TCG GTC CTG ACA AAA GAC AAG TTG
Met  Pro Glu Phe Leu Glu Asp Pro Ser Val Leu Thr Lys Asp Lys Leu
 -1  +1              5                   10                  15

AAG AGT GAG TTG GTC GCC AAC AAT GTG ACG CTG CCG GCC GGG GAG CAG
Lys Ser Glu Leu Val Ala Asn Asn Val Thr Leu Pro Ala Gly Glu Gln
             20                  25                  30

CGC AAA GAC GTG TAC GTC CAG CTC TAC CTG CAG CAC CTC ACG GCT CGC
Arg Lys Asp Val Tyr Val Gln Leu Tyr Leu Gln His Leu Thr Ala Arg
             35                  40                  45

AAC CGG CCG CCG CTC CCC GCC GGC ACC AAC AGC AAG GGG CCC CCG GAC
Asn Arg Pro Pro Leu Pro Ala Gly Thr Asn Ser Lys Gly Pro Pro Asp
         50                  55                  60

TTC TCC AGT GAC GAA GAG CGC GAG CCC ACC CCG GTC CTC GGC TCT GGG
Phe Ser Ser Asp Glu Glu Arg Glu Pro Thr Pro Val Leu Gly Ser Gly
         65                  70                  75

GCC GCC GCC GCG GGC CGG AGC CGA GCA GCC GTC GGC AGG AAA GCC ACA
Ala Ala Ala Ala Gly Arg Ser Arg Ala Ala Val Gly Arg Lys Ala Thr
 80              85                  90                      95

AAA AAA ACT GAT AAA CCC AGA CAA GAA GAT AAA GAT GAT CTA GAT GTA
Lys Lys Thr Asp Lys Pro Arg Gln Glu Asp Lys Asp Asp Leu Asp Val
                 100                 105                 110

ACA GAG CTC ACT AAT GAA GAT CTT TTG GAT CAG CTT GTG AAA TAC GGA
Thr Glu Leu Thr Asn Glu Asp Leu Leu Asp Gln Leu Val Lys Tyr Gly
             115                 120                 125

GTG AAT CCT GGT CCT ATT GTG GGA ACA ACC AGG AAG CTA TAT GAG AAA
Val Asn Pro Gly Pro Ile Val Gly Thr Thr Arg Lys Leu Tyr Glu Lys
             130                 135                 140
```

FIGURE 2B

```
AAG CTT TTG AAA CTG AGG GAA CAA GGA ACA GAA TCA AGA TCT TCT ACT
Lys Leu Leu Lys Leu Arg Glu Gln Gly Thr Glu Ser Arg Ser Ser Thr
    145             150             155

CCT CTG CCA ACA ATT TCT TCT TCA GCA GAA AAT ACA AGG CAG AAT GGA
Pro Leu Pro Thr Ile Ser Ser Ser Ala Glu Asn Thr Arg Gln Asn Gly
160             165             170             175

AGT AAT GAT TCT GAC AGA TAC AGT GAC AAT GAA GAA GAC TCT AAA ATA
Ser Asn Asp Ser Asp Arg Tyr Ser Asp Asn Glu Glu Asp Ser Lys Ile
            180             185    *          190

GAG CTC AAG CTT GAG AAG AGA GAA CCA CTA AAG GGC AGA GCA AAG ACT
Glu Leu Lys Leu Glu Lys Arg Glu Pro Leu Lys Gly Arg Ala Lys Thr
        195             200             205

CCA GTA ACA CTC AAG CAA AGA AGA GTT GAG CAC AAT CAG AGC TAT TCT
Pro Val Thr Leu Lys Gln Arg Arg Val Glu His Asn Gln Ser Tyr Ser
        210             215             220

CAA GCT GGA ATA ACT GAG ACT GAA TGG ACA AGT GGA TCT TCA AAA GGC
Gln Ala Gly Ile Thr Glu Thr Glu Trp Thr Ser Gly Ser Ser Lys Gly
        225             230             235

GGA CCT CTG CAG GCA TTA ACT AGG GAA TCT ACA AGA GGG TCA AGA AGA
Gly Pro Leu Gln Ala Leu Thr Arg Glu Ser Thr Arg Gly Ser Arg Arg
240             245             250             255

ACT CCA AGG AAA AGG GTG GAA ACT TCA GAA CAT TTT CGT ATA GAT GGT
Thr Pro Arg Lys Arg Val Glu Thr Ser Glu His Phe Arg Ile Asp Gly
            260             265             270

CCA GTA ATT TCA GAG AGT ACT CCC ATA GCT GAA ACT ATA ATG GCT TCA
Pro Val Ile Ser Glu Ser Thr Pro Ile Ala Glu Thr Ile Met Ala Ser
            275             280             285

AGC AAC GAA TCC TTA GTT GTC AAT AGG GTG ACT GGA AAT TTC AAG CAT
Ser Asn Glu Ser Leu Val Val Asn Arg Val Thr Gly Asn Phe Lys His
        290             295             300

GCA TCT CCT ATT CTG CCA ATC ACT GAA TTC TCA GAC ATA CCC AGA AGA
Ala Ser Pro Ile Leu Pro Ile Thr Glu Phe Ser Asp Ile Pro Arg Arg
    305             310             315

GCA CCA AAG AAA CCA TTG ACA AGA GCT GAA GTG GGA GAA AAA ACA GAG
Ala Pro Lys Lys Pro Leu Thr Arg Ala Glu Val Gly Glu Lys Thr Glu
320             325             330             335
```

FIGURE 2C

```
GAA AGA AGA GTA GAA AGG GAT ATT CTT AAG GAA ATG TTC CCC TAT GAA
Glu Arg Arg Val Glu Arg Asp Ile Leu Lys Glu Met Phe Pro Tyr Glu
            340             345                     350

GCA TCT ACA CCA ACA GGA ATT AGT GCT AGT TGC CGC AGA CCA ATC AAA
Ala Ser Thr Pro Thr Gly Ile Ser Ala Ser Cys Arg Arg Pro Ile Lys
            355             360                     365

GGG GCT GCA GGC CGG CCA TTA GAA CTC AGT GAT TTC AGG ATG GAG GAG
Gly Ala Ala Gly Arg Pro Leu Glu Leu Ser Asp Phe Arg Met Glu Glu
            370             375                     380

TCT TTT TCA TCT AAA TAT GTT CCT AAG TAT GTT CCC TTG GCA GAT GTC
Ser Phe Ser Ser Lys Tyr Val Pro Lys Tyr Val Pro Leu Ala Asp Val
    385                 390                 395

AAG TCA GAA AAG ACA AAA AAG GGA CGC TCC ATT CCC GTA TGG ATA AAA
Lys Ser Glu Lys Thr Lys Lys Gly Arg Ser Ile Pro Val Trp Ile Lys
400             405                 410                 415

ATT TTG CTG TTT GTT GTT GTG GCA GTT TTT TTG TTT TTG GTC TAT CAA
Ile Leu Leu Phe Val Val Val Ala Val Phe Leu Phe Leu Val Tyr Gln
            420                 425                 430

GCT ATG GAA ACC AAC CAA GTA AAT CCC TTC TCT AAT TTT CTT CAT GTT
Ala Met Glu Thr Asn Gln Val Asn Pro Phe Ser Asn Phe Leu His Val
            435                 440                 445

GAC CCT AGA AAA TCC AAC TGAATGGTAT CTCTTTGGCA CGTTCAACTT
Asp Pro Arg Lys Ser Asn
            450

GGTCTCCTAT TTTCAATAAC TGTTGAAAAA CATTTGTGTA CACTTGTTGA CTCCAAGAAC

TAAAAATAAT GTGATTTCGC CTCAATAAAT GTAGTATTTC ATTGAAAAGC AAAC
```

FIGURE 3A

DNA and Amino Acid Sequences of TP γ

CCCTGCTACC AAGGCCCAGC TATGGCCCCA GGGTTGAAAA GTTATGAGGG TCAGGGGTCT

TTTGTGTCCG GGTCTGGCTT GGCTTTGTGT CCGCGAGTTT TTGTTCCGCT CCGCAGCGCT

CTTCCCGGGC AGGAGCCGTG AGGCTCGGAG GCGGCAGCGC GGTCCCCGGC CAGGAGCAAG

CGCGCCGGCG TGAGCGGCGG CGGCAAAGGC TGTGGGGAGG GGGCTTCGCA GATCCCCGAG

```
    -1  +1
    ATG CCG GAG TTC CTG GAA GAC CCC TCG GTC CTG ACA AAA GAC AAG TTG
    Met Pro Glu Phe Leu Glu Asp Pro Ser Val Leu Thr Lys Asp Lys Leu
    -1  +1              5                   10                  15

AAG AGT GAG TTG GTC GCC AAC AAT GTG ACG CTG CCG GCC GGG GAG CAG
    Lys Ser Glu Leu Val Ala Asn Asn Val Thr Leu Pro Ala Gly Glu Gln
                    20                  25                  30

CGC AAA GAC GTG TAC GTC CAG CTC TAC CTG CAG CAC CTC ACG GCT CGC
    Arg Lys Asp Val Tyr Val Gln Leu Tyr Leu Gln His Leu Thr Ala Arg
                        35                  40                  45

AAC CGG CCG CCG CTC CCC GCC GGC ACC AAC AGC AAG GGG CCC CCG GAC
    Asn Arg Pro Pro Leu Pro Ala Gly Thr Asn Ser Lys Gly Pro Pro Asp
                    50                  55                  60

TTC TCC AGT GAC GAA GAG CGC GAG CCC ACC CCG GTC CTC GGC TCT GGG
    Phe Ser Ser Asp Glu Glu Arg Glu Pro Thr Pro Val Leu Gly Ser Gly
                65                  70                  75

GCC GCC GCC GCG GGC CGG AGC CGA GCA GCC GTC GGC AGG AAA GCC ACA
    Ala Ala Ala Ala Gly Arg Ser Arg Ala Ala Val Gly Arg Lys Ala Thr
    80                  85                  90                  95

AAA AAA ACT GAT AAA CCC AGA CAA GAA GAT AAA GAT GAT CTA GAT GTA
    Lys Lys Thr Asp Lys Pro Arg Gln Glu Asp Lys Asp Asp Leu Asp Val
                        100                 105                 110

ACA GAG CTC ACT AAT GAA GAT CTT TTG GAT CAG CTT GTG AAA TAC GGA
    Thr Glu Leu Thr Asn Glu Asp Leu Leu Asp Gln Leu Val Lys Tyr Gly
                    115                 120                 125

GTG AAT CCT GGT CCT ATT GTG GGA ACA ACC AGG AAG CTA TAT GAG AAA
    Val Asn Pro Gly Pro Ile Val Gly Thr Thr Arg Lys Leu Tyr Glu Lys
                130                 135                 140
```

FIGURE 3B

```
AAG CTT TTG AAA CTG AGG GAA CAA GGA ACA GAA TCA AGA TCT TCT ACT
Lys Leu Leu Lys Leu Arg Glu Gln Gly Thr Glu Ser Arg Ser Ser Thr
    145             150                 155

CCT CTG CCA ACA ATT TCT TCT TCA GCA GAA AAT ACA AGG CAG AAT GGA
Pro Leu Pro Thr Ile Ser Ser Ser Ala Glu Asn Thr Arg Gln Asn Gly
160             165                 170                 175

AGT AAT GAT TCT GAC AGA TAC AGT GAC AAT GAA GAA GAC TCT AAA ATA
Ser Asn Asp Ser Asp Arg Tyr Ser Asp Asn Glu Glu Asp Ser Lys Ile
                180                 185   *           190

C
GAG CTT AAG CTT GAG AAG AGA GAA CCA CTA AAG GGC AGA GCA AAG ACT
Glu Leu Lys Leu Glu Lys Arg Glu Pro Leu Lys Gly Arg Ala Lys Thr
            195                 200                 205

CCA GTA ACA CTC AAG CAA AGA AGA GTT GAG CAC AAT CAG GTG GGA GAA
Pro Val Thr Leu Lys Gln Arg Arg Val Glu His Asn Gln Val Gly Glu
        210                 215                 220

AAA ACA GAG GAA AGA AGA GTA GAA AGG GAT ATT CTT AAG GAA ATG TTC
Lys Thr Glu Glu Arg Arg Val Glu Arg Asp Ile Leu Lys Glu Met Phe
    225                 230                 235

CCC TAT GAA GCA TCT ACA CCA ACA GGA ATT AGT GCT AGT TGC CGC AGA
Pro Tyr Glu Ala Ser Thr Pro Thr Gly Ile Ser Ala Ser Cys Arg Arg
240                 245                 250                 255

CCA ATC AAA GGG GCT GCA GGC CGG CCA TTA GAA CTC AGT GAT TTC AGG
Pro Ile Lys Gly Ala Ala Gly Arg Pro Leu Glu Leu Ser Asp Phe Arg
                260                 265                 270

ATG GAG GAG TCT TTT TCA TCT AAA TAT GTT CCT AAG TAT GTT CCC TTG
Met Glu Glu Ser Phe Ser Ser Lys Tyr Val Pro Lys Tyr Val Pro Leu
            275                 280                 285

GCA GAT GTC AAG TCA GAA AAG ACA AAA AAG GGA CGC TCC ATT CCC GTA
Ala Asp Val Lys Ser Glu Lys Thr Lys Lys Gly Arg Ser Ile Pro Val
        290                 295                 300

TGG ATA AAA ATT TTG CTG TTT GTT GTT GTG GCA GTT TTT TTG TTT TTG
Trp Ile Lys Ile Leu Leu Phe Val Val Val Ala Val Phe Leu Phe Leu
    305                 310                 315

GTC TAT CAA GCT ATG GAA ACC AAC CAA GTA AAT CCC TTC TCT AAT TTT
Val Tyr Gln Ala Met Glu Thr Asn Gln Val Asn Pro Phe Ser Asn Phe
320                 325                 330                 335

CTT CAT GTT GAC CCT AGA AAA TCC AAC TGA ATGGTAT CTCTTTGGCA
Leu His Val Asp Pro Arg Lys Ser Asn
                340
```

FIGURE 3C

CGTTCAACTT GGTCTCCTAT TTTCAATAAC TGTTGAAAAA CATTTGTGTA CACTTGTTGA
CTCCAAGAAC TAAAAATAAT GTGATTTCGC CTCAATAAAT GTAGTATTTC ATTGAAAAGC
AAACAAAATA TATATAAATG GACTTCATTA AAATGTTTTT GAACTTTGGA CTAGTAGGAG
ATCACTTTGT GCCATATGAA TAATCTTTTT TAGCTCTGGA ACTTTTTGTA GGCTTTATTT
TTTTAATGTG GGCATCTTAT TTCATTTTTG AAAAAATGTA TATGTTTTTT GTGTATTTGG
GAAACGAAGG GTGAAACATG GTAGTATAAT GTGAAGCTAC ACATTTAAAT ACTTAGAATT
CTTACAGAAA AGATTTTAAG AATTATTCTC TGCTGAATAA AAACTGCAAA TATGTGAAAC
ATAATGAAAT TCAGTAAGAG GAAAAGTAAC TTGGTTGTAC TTTTTGTAAC TGCAACAAAG
TTTGATGGTG TTTATGAGGA AAAGTACAGC AATAATCTCT TCTGTAACCT TTATTAATAG
TAATGTTGTT GTAGCCCTAT CATACTCACT TTTTAAGACA CAGTATCATG AAAGTCCTAT
TTCAGTAAGA CCCATTTACA TACAGTAGAT TTTTAGCAGA GATCTTTTAG TGTAACATAC
ATATTTTAGA GAATTGTTGG CTAGCTGTAC ATGTTTTGAA AAGCTGTTTA GCTAGCTATA
AGGCTATAAT TGGAAATTTG TATTTTTTAT TTACAGCAAA ACATTTATTC AGTCATCCAG
TTTGCTACCA AAATATGTTT TAGATAAGTG TGTGTATGTT TGTTTAGAAG TTAGAAATTG
TAAACACTGG TCTTATGTTT CATTTGGATT CATTATTGCA TTGTCTTGTT ACCAGAAACA
AATTTTGCCG AGCTTTTTTT GCCCTATATT TCCAGCATA ATTTGATTAG AAAGTACAAA
AAGGGCCGGG CGCGGTGGCT TACGCCTGTA ATCCCAGCAC TTTGGGAGGC CAGGGCGGGT
GGATCACGAG GTCAGGAGAT CGGGACCATC CTGGCCAACA TGGTGAAACC CCGTCTCTAC
TAAAAAAAAA AAAAAA

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 2490 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 205..2286

( x i ) SEQUENCE DESCRIPTION: SEQ ID NO:1:

```
GTTCGTAGTT  CGGCTCTGGG  GTCTTTTGTG  TCCGGGTCTG  GCTTGGCTTT  GTGTCCGCGA                          60

GTTTTTGTTC  CGCTCCGCAG  CGCTCTTCCC  GGGCAGGAGC  CGTGAGGCTC  GGAGGCGGCA                         120

GCGCGGTCCC  CGGCCAGGAG  CAAGCGCGCC  GGCGTGAGCG  GCGGCGGCAA  AGGCTGTGGG                         180

GAGGGGGCTT  CGCAGATCCC  CGAG ATG CCG GAG TTC CTG GAA GAC CCC TCG                              231
                             Met Pro Glu Phe Leu Glu Asp Pro Ser
                              1               5

GTC CTG ACA AAA GAC AAG TTG AAG AGT GAG TTG GTC GCC AAC AAT GTG                               279
Val Leu Thr Lys Asp Lys Leu Lys Ser Glu Leu Val Ala Asn Asn Val
 10              15                  20                  25

ACG CTG CCG GCC GGG GAG CAG CGC AAA GAC GTG TAC GTC CAG CTC TAC                               327
Thr Leu Pro Ala Gly Glu Gln Arg Lys Asp Val Tyr Val Gln Leu Tyr
                 30                  35                  40

CTG CAG CAC CTC ACG GCT CGC AAC CGG CCG CCG CTC CCC GCC GGC ACC                               375
Leu Gln His Leu Thr Ala Arg Asn Arg Pro Pro Leu Pro Ala Gly Thr
             45                  50                  55

AAC AGC AAG GGG CCC CCG GAC TTC TCC AGT GAC GAA GAG CGC GAG CCC                               423
Asn Ser Lys Gly Pro Pro Asp Phe Ser Ser Asp Glu Glu Arg Glu Pro
         60                  65                  70

ACC CCG GTC CTC GGC TCT GGG GCC GCC GCC GCG GGC CGG AGC CGA GCA                               471
Thr Pro Val Leu Gly Ser Gly Ala Ala Ala Ala Gly Arg Ser Arg Ala
     75                  80                  85

GCC GTC GGC AGG AAA GCC ACA AAA AAA ACT GAT AAA CCC AGA CAA GAA                               519
Ala Val Gly Arg Lys Ala Thr Lys Lys Thr Asp Lys Pro Arg Gln Glu
 90                  95                 100                 105

GAT AAA GAT GAT CTA GAT GTA ACA GAG CTC ACT AAT GAA GAT CTT TTG                               567
Asp Lys Asp Asp Leu Asp Val Thr Glu Leu Thr Asn Glu Asp Leu Leu
                110                 115                 120

GAT CAG CTT GTG AAA TAC GGA GTG AAT CCT GGT CCT ATT GTG GGA ACA                               615
Asp Gln Leu Val Lys Tyr Gly Val Asn Pro Gly Pro Ile Val Gly Thr
            125                 130                 135

ACC AGG AAG CTA TAT GAG AAA AAG CTT TTG AAA CTG AGG GAA CAA GGA                               663
```

```
Thr Arg Lys Leu Tyr Glu Lys Lys Leu Leu Lys Leu Arg Glu Gln Gly
    140             145             150

ACA GAA TCA AGA TCT TCT ACT CCT CTG CCA ACA ATT TCT TCT TCA GCA      711
Thr Glu Ser Arg Ser Ser Thr Pro Leu Pro Thr Ile Ser Ser Ser Ala
    155             160             165

GAA AAT ACA AGG CAG AAT GGA AGT AAT GAT TCT GAC AGA TAC AGT GAC      759
Glu Asn Thr Arg Gln Asn Gly Ser Asn Asp Ser Asp Arg Tyr Ser Asp
170             175             180             185

AAT GAA GAA GGA AAG AAG AAA GAA CAC AAG AAA GTG AAG TCC ACT AGG      807
Asn Glu Glu Gly Lys Lys Lys Glu His Lys Lys Val Lys Ser Thr Arg
            190             195             200

GAT ATT GTT CCT TTT TCT GAA CTT GGA ACT ACT CCC TCT GGT GGT GGA      855
Asp Ile Val Pro Phe Ser Glu Leu Gly Thr Thr Pro Ser Gly Gly Gly
            205             210             215

TTT TTT CAG GGT ATT TCT TTT CCT GAA ATC TCC ACC CGT CCT CCT TTG      903
Phe Phe Gln Gly Ile Ser Phe Pro Glu Ile Ser Thr Arg Pro Pro Leu
        220             225             230

GGC AGT ACC GAA CTA CAG GCA GCT AAG AAA GTA CAT ACT TCT AAG GGA      951
Gly Ser Thr Glu Leu Gln Ala Ala Lys Lys Val His Thr Ser Lys Gly
        235             240             245

GAC CTA CCT AGG GAG CCT CTT GTT GCC ACA AAC TTG CCT GGC AGG GGA      999
Asp Leu Pro Arg Glu Pro Leu Val Ala Thr Asn Leu Pro Gly Arg Gly
250             255             260             265

CAG TTG CAG AAG TTA GCC TCT GAA AGG AAT TTG TTT ATT TCA TGC AAG     1047
Gln Leu Gln Lys Leu Ala Ser Glu Arg Asn Leu Phe Ile Ser Cys Lys
            270             275             280

TCT AGC CAT GAT AGG TGT TTA GAG AAA AGT TCT TCG TCA TCT TCT CAG     1095
Ser Ser His Asp Arg Cys Leu Glu Lys Ser Ser Ser Ser Ser Ser Gln
            285             290             295

CCT GAA CAC AGT GCC ATG TTG GTC TCT ACT GCA GCT TCT CCT TCA CTG     1143
Pro Glu His Ser Ala Met Leu Val Ser Thr Ala Ala Ser Pro Ser Leu
        300             305             310

ATT AAA GAA ACC ACC ACT GGT TAC TAT AAA GAC ATA GTA GAA AAT ATT     1191
Ile Lys Glu Thr Thr Thr Gly Tyr Tyr Lys Asp Ile Val Glu Asn Ile
    315             320             325

TGC GGT AGA GAG AAA AGT GGA ATT CAA CCA TTA TGT CCT GAG AGG TCC     1239
Cys Gly Arg Glu Lys Ser Gly Ile Gln Pro Leu Cys Pro Glu Arg Ser
330             335             340             345

CAT ATT TCA GAT CAA TCG CCT CTC TCC AGT AAA AGG AAA GCA CTA GAA     1287
His Ile Ser Asp Gln Ser Pro Leu Ser Ser Lys Arg Lys Ala Leu Glu
            350             355             360

GAG TCT GAG AGC TCA CAA CTA ATT TCT CCG CCA CTT GCC CAG GCA ATC     1335
Glu Ser Glu Ser Ser Gln Leu Ile Ser Pro Pro Leu Ala Gln Ala Ile
            365             370             375

AGA GAT TAT GTC AAT TCT CTG TTG GTC CAG GGT GGG GTA GGT AGT TTG     1383
Arg Asp Tyr Val Asn Ser Leu Leu Val Gln Gly Gly Val Gly Ser Leu
        380             385             390

CCT GGA ACT TCT AAC TCT ATG CCC CCA CTG GAT GTA GAA AAC ATA CAG     1431
Pro Gly Thr Ser Asn Ser Met Pro Pro Leu Asp Val Glu Asn Ile Gln
        395             400             405

AAG AGA ATT GAT CAG TCT AAG TTT CAA GAA ACT GAA TTC CTG TCT CCT     1479
Lys Arg Ile Asp Gln Ser Lys Phe Gln Glu Thr Glu Phe Leu Ser Pro
410             415             420             425

CCA AGA AAA GTC CCT AGA CTG AGT GAG AAG TCA GTG GAG GAA AGG GAT     1527
Pro Arg Lys Val Pro Arg Leu Ser Glu Lys Ser Val Glu Glu Arg Asp
            430             435             440

TCA GGT TCC TTT GTG GCA TTT CAG AAC ATA CCT GGA TCC GAA CTG ATG     1575
Ser Gly Ser Phe Val Ala Phe Gln Asn Ile Pro Gly Ser Glu Leu Met
            445             450             455
```

-continued

```
TCT TCT TTT GCC AAA ACT GTT GTC TCT CAT TCA CTC ACT ACC TTA GGT    1623
Ser Ser Phe Ala Lys Thr Val Val Ser His Ser Leu Thr Thr Leu Gly
        460             465                 470

CTA GAA GTG GCT AAG CAA TCA CAG CAT GAT AAA ATA GAT GCC TCA GAA    1671
Leu Glu Val Ala Lys Gln Ser Gln His Asp Lys Ile Asp Ala Ser Glu
    475             480                 485

CTA TCT TTT CCC TTC CAT GAA TCT ATT TTA AAA GTA ATT GAA GAA GAA    1719
Leu Ser Phe Pro Phe His Glu Ser Ile Leu Lys Val Ile Glu Glu Glu
490             495                 500                 505

TGG CAG CAA GTT GAC AGG CAG CTG CCT TCA CTG GCA TGC AAA TAT CCA    1767
Trp Gln Gln Val Asp Arg Gln Leu Pro Ser Leu Ala Cys Lys Tyr Pro
                510             515                 520

GTT TCT TCC AGG GAG GCA ACA CAG ATA TTA TCA GTT CCA AAA GTA GAT    1815
Val Ser Ser Arg Glu Ala Thr Gln Ile Leu Ser Val Pro Lys Val Asp
            525             530                 535

GAT GAA ATC CTA GGG TTT ATT TCT GAA GCC ACT CCA CTA GGA GGT ATT    1863
Asp Glu Ile Leu Gly Phe Ile Ser Glu Ala Thr Pro Leu Gly Gly Ile
        540             545                 550

CAA GCA GCC TCC ACT GAG TCT TGC AAT CAG CAG TTG GAC TTA GCA CTC    1911
Gln Ala Ala Ser Thr Glu Ser Cys Asn Gln Gln Leu Asp Leu Ala Leu
    555             560                 565

TGT AGA GCA TAT GAA GCT GCA GCA TCA GCA TTG CAG ATT GCA ACT CAC    1959
Cys Arg Ala Tyr Glu Ala Ala Ala Ser Ala Leu Gln Ile Ala Thr His
570             575                 580                 585

ACT GCC TTT GTA GCT AAG GCT ATG CAG GCA GAC ATT AGT CAA GCT GCA    2007
Thr Ala Phe Val Ala Lys Ala Met Gln Ala Asp Ile Ser Gln Ala Ala
                590             595                 600

CAG ATT CTT AGC TCA GAT CCT AGT CGT ACC CAC CAA GCG CTT GGG ATT    2055
Gln Ile Leu Ser Ser Asp Pro Ser Arg Thr His Gln Ala Leu Gly Ile
            605             610                 615

CTG AGC AAA ACA TAT GAT GCA GCC TCA TAT ATT TGT GAA GCT GCA TTT    2103
Leu Ser Lys Thr Tyr Asp Ala Ala Ser Tyr Ile Cys Glu Ala Ala Phe
        620             625                 630

GAT GAA GTG AAG ATG GCT GCC CAT ACC ATG GGA AAT GCC ACT GTA GGT    2151
Asp Glu Val Lys Met Ala Ala His Thr Met Gly Asn Ala Thr Val Gly
    635             640                 645

CGT CGA TAC CTC TGG CTG AAG GAT TGC AAA ATT AAT TTA GCT TCT AAG    2199
Arg Arg Tyr Leu Trp Leu Lys Asp Cys Lys Ile Asn Leu Ala Ser Lys
650             655                 660                 665

AAT AAG CTG GCT TCC ACT CCC TTT AAA GGT GGA ACA TTA TTT GGA GGA    2247
Asn Lys Leu Ala Ser Thr Pro Phe Lys Gly Gly Thr Leu Phe Gly Gly
                670             675                 680

GAA GTA TGC AAA GTA ATT AAA AAG CGT GGA AAT AAA CAC TAGTAAAATT    2296
Glu Val Cys Lys Val Ile Lys Lys Arg Gly Asn Lys His
            685             690

AAGGACAAAA AGACATCTAT CTTATCTTTC AGGTACTTTA TGCCAACATT TTCTTTTCTG    2356

TTAAGGTTGT TTTAGTTTCC AGATAGGGCT AATTACAAAA TGTTAAGCTT CTACCCATCA    2416

AATTACAGTA TAAAAGTAAT TGCCTGTGTA GAACTACTTG TCTTTTCTAA AGATTTGCGT    2476

AGATAGGAAG CCTG                                                      2490
```

( 2 ) INFORMATION FOR SEQ ID NO:2:

( i ) SEQUENCE CHARACTERISTICS:
        ( A ) LENGTH: 694 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

-continued

| | | | | | | | | | | | | | | |
|---|---|---|---|---|---|---|---|---|---|---|---|---|---|---|
| Met<br>1 | Pro | Glu | Phe | Leu<br>5 | Glu | Asp | Pro | Ser | Val<br>10 | Leu | Thr | Lys | Asp | Leu<br>15 |
| Lys | Ser | Glu | Leu<br>20 | Val | Ala | Asn | Asn | Val<br>25 | Thr | Leu | Pro | Ala | Gly<br>30 | Glu | Gln |
| Arg | Lys | Asp<br>35 | Val | Tyr | Val | Gln | Leu<br>40 | Tyr | Leu | Gln | His | Leu<br>45 | Thr | Ala | Arg |
| Asn | Arg<br>50 | Pro | Pro | Leu | Pro<br>55 | Ala | Gly | Thr | Asn | Ser<br>60 | Lys | Gly | Pro | Pro | Asp |
| Phe<br>65 | Ser | Ser | Asp | Glu | Glu<br>70 | Arg | Glu | Pro | Thr | Pro<br>75 | Val | Leu | Gly | Ser | Gly<br>80 |
| Ala | Ala | Ala | Ala | Gly<br>85 | Arg | Ser | Arg | Ala | Ala<br>90 | Val | Gly | Arg | Lys | Ala<br>95 | Thr |
| Lys | Lys | Thr | Asp<br>100 | Lys | Pro | Arg | Gln | Glu<br>105 | Asp | Lys | Asp | Asp | Leu<br>110 | Asp | Val |
| Thr | Glu | Leu<br>115 | Thr | Asn | Glu | Asp | Leu<br>120 | Leu | Asp | Gln | Leu | Val<br>125 | Lys | Tyr | Gly |
| Val | Asn<br>130 | Pro | Gly | Pro | Ile | Val<br>135 | Gly | Thr | Thr | Arg | Lys<br>140 | Leu | Tyr | Glu | Lys |
| Lys<br>145 | Leu | Leu | Lys | Leu | Arg<br>150 | Glu | Gln | Gly | Thr | Glu<br>155 | Ser | Arg | Ser | Ser | Thr<br>160 |
| Pro | Leu | Pro | Thr | Ile<br>165 | Ser | Ser | Ser | Ala | Glu<br>170 | Asn | Thr | Arg | Gln | Asn<br>175 | Gly |
| Ser | Asn | Asp | Ser<br>180 | Asp | Arg | Tyr | Ser | Asp<br>185 | Asn | Glu | Glu | Gly | Lys<br>190 | Lys | Lys |
| Glu | His | Lys<br>195 | Lys | Val | Lys | Ser | Thr<br>200 | Arg | Asp | Ile | Val | Pro<br>205 | Phe | Ser | Glu |
| Leu | Gly<br>210 | Thr | Thr | Pro | Ser | Gly<br>215 | Gly | Gly | Phe | Phe | Gln<br>220 | Gly | Ile | Ser | Phe |
| Pro<br>225 | Glu | Ile | Ser | Thr | Arg<br>230 | Pro | Pro | Leu | Gly | Ser<br>235 | Thr | Glu | Leu | Gln | Ala<br>240 |
| Ala | Lys | Lys | Val | His<br>245 | Thr | Ser | Lys | Gly | Asp<br>250 | Leu | Pro | Arg | Glu | Pro<br>255 | Leu |
| Val | Ala | Thr | Asn<br>260 | Leu | Pro | Gly | Arg | Gly<br>265 | Gln | Leu | Gln | Lys | Leu<br>270 | Ala | Ser |
| Glu | Arg | Asn<br>275 | Leu | Phe | Ile | Ser | Cys<br>280 | Lys | Ser | Ser | His | Asp<br>285 | Arg | Cys | Leu |
| Glu | Lys<br>290 | Ser | Ser | Ser | Ser | Ser<br>295 | Ser | Gln | Pro | Glu | His<br>300 | Ser | Ala | Met | Leu |
| Val<br>305 | Ser | Thr | Ala | Ala | Ser<br>310 | Pro | Ser | Leu | Ile | Lys<br>315 | Glu | Thr | Thr | Thr | Gly<br>320 |
| Tyr | Tyr | Lys | Asp | Ile<br>325 | Val | Glu | Asn | Ile | Cys<br>330 | Gly | Arg | Glu | Lys | Ser<br>335 | Gly |
| Ile | Gln | Pro | Leu<br>340 | Cys | Pro | Glu | Arg | Ser<br>345 | His | Ile | Ser | Asp | Gln<br>350 | Ser | Pro |
| Leu | Ser | Ser<br>355 | Lys | Arg | Lys | Ala | Leu<br>360 | Glu | Glu | Ser | Glu | Ser<br>365 | Ser | Gln | Leu |
| Ile | Ser<br>370 | Pro | Pro | Leu | Ala | Gln<br>375 | Ala | Ile | Arg | Asp | Tyr<br>380 | Val | Asn | Ser | Leu |
| Leu<br>385 | Val | Gln | Gly | Gly | Val<br>390 | Gly | Ser | Leu | Pro | Gly<br>395 | Thr | Ser | Asn | Ser | Met<br>400 |
| Pro | Pro | Leu | Asp | Val<br>405 | Glu | Asn | Ile | Gln | Lys<br>410 | Arg | Ile | Asp | Gln | Ser<br>415 | Lys |

-continued

| | | | | | | | | | | | | | |
|---|---|---|---|---|---|---|---|---|---|---|---|---|---|
| Phe | Gln | Glu | Thr 420 | Glu | Phe | Leu | Ser | Pro 425 | Pro | Arg | Lys | Val | Pro 430 | Arg | Leu |
| Ser | Glu | Lys 435 | Ser | Val | Glu | Glu | Arg 440 | Asp | Ser | Gly | Ser | Phe 445 | Val | Ala | Phe |
| Gln | Asn 450 | Ile | Pro | Gly | Ser 455 | Glu | Leu | Met | Ser | Ser | Phe 460 | Ala | Lys | Thr | Val |
| Val 465 | Ser | His | Ser | Leu | Thr 470 | Thr | Leu | Gly | Leu | Glu 475 | Val | Ala | Lys | Gln | Ser 480 |
| Gln | His | Asp | Lys | Ile 485 | Asp | Ala | Ser | Glu | Leu 490 | Ser | Phe | Pro | Phe | His 495 | Glu |
| Ser | Ile | Leu | Lys 500 | Val | Ile | Glu | Glu | Trp 505 | Gln | Gln | Val | Asp 510 | Arg | Gln |
| Leu | Pro | Ser 515 | Leu | Ala | Cys | Lys | Tyr 520 | Pro | Val | Ser | Ser | Arg 525 | Glu | Ala | Thr |
| Gln | Ile 530 | Leu | Ser | Val | Pro | Lys 535 | Val | Asp | Asp | Glu | Ile 540 | Leu | Gly | Phe | Ile |
| Ser 545 | Glu | Ala | Thr | Pro | Leu 550 | Gly | Gly | Ile | Gln | Ala 555 | Ala | Ser | Thr | Glu | Ser 560 |
| Cys | Asn | Gln | Gln | Leu 565 | Asp | Leu | Ala | Leu | Cys 570 | Arg | Ala | Tyr | Glu | Ala 575 | Ala |
| Ala | Ser | Ala | Leu 580 | Gln | Ile | Ala | Thr | His 585 | Thr | Ala | Phe | Val | Ala 590 | Lys | Ala |
| Met | Gln | Ala 595 | Asp | Ile | Ser | Gln | Ala 600 | Ala | Gln | Ile | Leu | Ser 605 | Ser | Asp | Pro |
| Ser | Arg 610 | Thr | His | Gln | Ala | Leu 615 | Gly | Ile | Leu | Ser | Lys 620 | Thr | Tyr | Asp | Ala |
| Ala 625 | Ser | Tyr | Ile | Cys | Glu 630 | Ala | Ala | Phe | Asp | Glu 635 | Val | Lys | Met | Ala | Ala 640 |
| His | Thr | Met | Gly | Asn 645 | Ala | Thr | Val | Gly | Arg 650 | Arg | Tyr | Leu | Trp | Leu 655 | Lys |
| Asp | Cys | Lys | Ile 660 | Asn | Leu | Ala | Ser | Lys 665 | Asn | Lys | Leu | Ala | Ser 670 | Thr | Pro |
| Phe | Lys | Gly 675 | Gly | Thr | Leu | Phe | Gly 680 | Gly | Glu | Val | Cys | Lys 685 | Val | Ile | Lys |
| Lys | Arg 690 | Gly | Asn | Lys | His | | | | | | | | | | |

( 2 ) INFORMATION FOR SEQ ID NO:3:

( i ) SEQUENCE CHARACTERISTICS:
        ( A ) LENGTH: 1743 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 238..1599

( x i ) SEQUENCE DESCRIPTION: SEQ ID NO:3:

```
GGTTGGTGCG AGCTTCCAGC TTGGCCGCAG TTGGTTCGTA GTTCGGCTCT GGGGTCTTTT      60

GTGTCCGGGT CTGGCTTGGC TTTGTGTCCG CGAGTTTTTG TTCCGCTCCG CAGCGCTCTT     120

CCCGGGCAGG AGCCGTGAGG CTCGGAGGCG GCAGCGCGGT CCCCGGCCAG GAGCAAGCGC     180

GCCGGCGTGA GCGGCGGCGG CAAAGGCTGT GGGGAGGGGG CTTCGCAGAT CCCCGAG        237
```

| | | | | | | | | | | | | | | | | |
|---|---|---|---|---|---|---|---|---|---|---|---|---|---|---|---|---|
| ATG | CCG | GAG | TTC | CTG | GAA | GAC | CCC | TCG | GTC | CTG | ACA | AAA | GAC | AAG | TTG | 285 |
| Met | Pro | Glu | Phe | Leu | Glu | Asp | Pro | Ser | Val | Leu | Thr | Lys | Asp | Lys | Leu | |
| 1 | | | | 5 | | | | | 10 | | | | | 15 | | |
| AAG | AGT | GAG | TTG | GTC | GCC | AAC | AAT | GTG | ACG | CTG | CCG | GCC | GGG | GAG | CAG | 333 |
| Lys | Ser | Glu | Leu | Val | Ala | Asn | Asn | Val | Thr | Leu | Pro | Ala | Gly | Glu | Gln | |
| | | | 20 | | | | | 25 | | | | | 30 | | | |
| CGC | AAA | GAC | GTG | TAC | GTC | CAG | CTC | TAC | CTG | CAG | CAC | CTC | ACG | GCT | CGC | 381 |
| Arg | Lys | Asp | Val | Tyr | Val | Gln | Leu | Tyr | Leu | Gln | His | Leu | Thr | Ala | Arg | |
| | | 35 | | | | | 40 | | | | | 45 | | | | |
| AAC | CGG | CCG | CCG | CTC | CCC | GCC | GGC | ACC | AAC | AGC | AAG | GGG | CCC | CCG | GAC | 429 |
| Asn | Arg | Pro | Pro | Leu | Pro | Ala | Gly | Thr | Asn | Ser | Lys | Gly | Pro | Pro | Asp | |
| | 50 | | | | | 55 | | | | | 60 | | | | | |
| TTC | TCC | AGT | GAC | GAA | GAG | CGC | GAG | CCC | ACC | CCG | GTC | CTC | GGC | TCT | GGG | 477 |
| Phe | Ser | Ser | Asp | Glu | Glu | Arg | Glu | Pro | Thr | Pro | Val | Leu | Gly | Ser | Gly | |
| 65 | | | | | 70 | | | | | 75 | | | | | 80 | |
| GCC | GCC | GCC | GCG | GGC | CGG | AGC | CGA | GCA | GCC | GTC | GGC | AGG | AAA | GCC | ACA | 525 |
| Ala | Ala | Ala | Ala | Gly | Arg | Ser | Arg | Ala | Ala | Val | Gly | Arg | Lys | Ala | Thr | |
| | | | | 85 | | | | | 90 | | | | | 95 | | |
| AAA | AAA | ACT | GAT | AAA | CCC | AGA | CAA | GAA | GAT | AAA | GAT | GAT | CTA | GAT | GTA | 573 |
| Lys | Lys | Thr | Asp | Lys | Pro | Arg | Gln | Glu | Asp | Lys | Asp | Asp | Leu | Asp | Val | |
| | | | 100 | | | | | 105 | | | | | 110 | | | |
| ACA | GAG | CTC | ACT | AAT | GAA | GAT | CTT | TTG | GAT | CAG | CTT | GTG | AAA | TAC | GGA | 621 |
| Thr | Glu | Leu | Thr | Asn | Glu | Asp | Leu | Leu | Asp | Gln | Leu | Val | Lys | Tyr | Gly | |
| | | 115 | | | | | 120 | | | | | 125 | | | | |
| GTG | AAT | CCT | GGT | CCT | ATT | GTG | GGA | ACA | ACC | AGG | AAG | CTA | TAT | GAG | AAA | 669 |
| Val | Asn | Pro | Gly | Pro | Ile | Val | Gly | Thr | Thr | Arg | Lys | Leu | Tyr | Glu | Lys | |
| | 130 | | | | | 135 | | | | | 140 | | | | | |
| AAG | CTT | TTG | AAA | CTG | AGG | GAA | CAA | GGA | ACA | GAA | TCA | AGA | TCT | TCT | ACT | 717 |
| Lys | Leu | Leu | Lys | Leu | Arg | Glu | Gln | Gly | Thr | Glu | Ser | Arg | Ser | Ser | Thr | |
| 145 | | | | | 150 | | | | | 155 | | | | | 160 | |
| CCT | CTG | CCA | ACA | ATT | TCT | TCT | TCA | GCA | GAA | AAT | ACA | AGG | CAG | AAT | GGA | 765 |
| Pro | Leu | Pro | Thr | Ile | Ser | Ser | Ser | Ala | Glu | Asn | Thr | Arg | Gln | Asn | Gly | |
| | | | | 165 | | | | | 170 | | | | | 175 | | |
| AGT | AAT | GAT | TCT | GAC | AGA | TAC | AGT | GAC | AAT | GAA | GAA | GAC | TCT | AAA | ATA | 813 |
| Ser | Asn | Asp | Ser | Asp | Arg | Tyr | Ser | Asp | Asn | Glu | Glu | Asp | Ser | Lys | Ile | |
| | | | 180 | | | | | 185 | | | | | 190 | | | |
| GAG | CTC | AAG | CTT | GAG | AAG | AGA | GAA | CCA | CTA | AAG | GGC | AGA | GCA | AAG | ACT | 861 |
| Glu | Leu | Lys | Leu | Glu | Lys | Arg | Glu | Pro | Leu | Lys | Gly | Arg | Ala | Lys | Thr | |
| | | 195 | | | | | 200 | | | | | 205 | | | | |
| CCA | GTA | ACA | CTC | AAG | CAA | AGA | AGA | GTT | GAG | CAC | AAT | CAG | AGC | TAT | TCT | 909 |
| Pro | Val | Thr | Leu | Lys | Gln | Arg | Arg | Val | Glu | His | Asn | Gln | Ser | Tyr | Ser | |
| | 210 | | | | | 215 | | | | | 220 | | | | | |
| CAA | GCT | GGA | ATA | ACT | GAG | ACT | GAA | TGG | ACA | AGT | GGA | TCT | TCA | AAA | GGC | 957 |
| Gln | Ala | Gly | Ile | Thr | Glu | Thr | Glu | Trp | Thr | Ser | Gly | Ser | Ser | Lys | Gly | |
| 225 | | | | | 230 | | | | | 235 | | | | | 240 | |
| GGA | CCT | CTG | CAG | GCA | TTA | ACT | AGG | GAA | TCT | ACA | AGA | GGG | TCA | AGA | AGA | 1005 |
| Gly | Pro | Leu | Gln | Ala | Leu | Thr | Arg | Glu | Ser | Thr | Arg | Gly | Ser | Arg | Arg | |
| | | | | 245 | | | | | 250 | | | | | 255 | | |
| ACT | CCA | AGG | AAA | AGG | GTG | GAA | ACT | TCA | GAA | CAT | TTT | CGT | ATA | GAT | GGT | 1053 |
| Thr | Pro | Arg | Lys | Arg | Val | Glu | Thr | Ser | Glu | His | Phe | Arg | Ile | Asp | Gly | |
| | | | 260 | | | | | 265 | | | | | 270 | | | |
| CCA | GTA | ATT | TCA | GAG | AGT | ACT | CCC | ATA | GCT | GAA | ACT | ATA | ATG | GCT | TCA | 1101 |
| Pro | Val | Ile | Ser | Glu | Ser | Thr | Pro | Ile | Ala | Glu | Thr | Ile | Met | Ala | Ser | |
| | | 275 | | | | | 280 | | | | | 285 | | | | |
| AGC | AAC | GAA | TCC | TTA | GTT | GTC | AAT | AGG | GTG | ACT | GGA | AAT | TTC | AAG | CAT | 1149 |
| Ser | Asn | Glu | Ser | Leu | Val | Val | Asn | Arg | Val | Thr | Gly | Asn | Phe | Lys | His | |
| | 290 | | | | | 295 | | | | | 300 | | | | | |
| GCA | TCT | CCT | ATT | CTG | CCA | ATC | ACT | GAA | TTC | TCA | GAC | ATA | CCC | AGA | AGA | 1197 |
| Ala | Ser | Pro | Ile | Leu | Pro | Ile | Thr | Glu | Phe | Ser | Asp | Ile | Pro | Arg | Arg | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| GCA | CCA | AAG | AAA | CCA | TTG | ACA | AGA | GCT | GAA | GTG | GGA | GAA | AAA | ACA | GAG | 1245 |
| Ala | Pro | Lys | Lys | Pro | Leu | Thr | Arg | Ala | Glu | Val | Gly | Glu | Lys | Thr | Glu | |
| | | | | 325 | | | | | 330 | | | | | 335 | | |
| GAA | AGA | AGA | GTA | GAA | AGG | GAT | ATT | CTT | AAG | GAA | ATG | TTC | CCC | TAT | GAA | 1293 |
| Glu | Arg | Arg | Val | Glu | Arg | Asp | Ile | Leu | Lys | Glu | Met | Phe | Pro | Tyr | Glu | |
| | | | 340 | | | | | 345 | | | | | 350 | | | |
| GCA | TCT | ACA | CCA | ACA | GGA | ATT | AGT | GCT | AGT | TGC | CGC | AGA | CCA | ATC | AAA | 1341 |
| Ala | Ser | Thr | Pro | Thr | Gly | Ile | Ser | Ala | Ser | Cys | Arg | Arg | Pro | Ile | Lys | |
| | | 355 | | | | | 360 | | | | | 365 | | | | |
| GGG | GCT | GCA | GGC | CGG | CCA | TTA | GAA | CTC | AGT | GAT | TTC | AGG | ATG | GAG | GAG | 1389 |
| Gly | Ala | Ala | Gly | Arg | Pro | Leu | Glu | Leu | Ser | Asp | Phe | Arg | Met | Glu | Glu | |
| | 370 | | | | | 375 | | | | | 380 | | | | | |
| TCT | TTT | TCA | TCT | AAA | TAT | GTT | CCT | AAG | TAT | GTT | CCC | TTG | GCA | GAT | GTC | 1437 |
| Ser | Phe | Ser | Ser | Lys | Tyr | Val | Pro | Lys | Tyr | Val | Pro | Leu | Ala | Asp | Val | |
| 385 | | | | | 390 | | | | | 395 | | | | | 400 | |
| AAG | TCA | GAA | AAG | ACA | AAA | AAG | GGA | CGC | TCC | ATT | CCC | GTA | TGG | ATA | AAA | 1485 |
| Lys | Ser | Glu | Lys | Thr | Lys | Lys | Gly | Arg | Ser | Ile | Pro | Val | Trp | Ile | Lys | |
| | | | | 405 | | | | | 410 | | | | | 415 | | |
| ATT | TTG | CTG | TTT | GTT | GTT | GTG | GCA | GTT | TTT | TTG | TTT | TTG | GTC | TAT | CAA | 1533 |
| Ile | Leu | Leu | Phe | Val | Val | Val | Ala | Val | Phe | Leu | Phe | Leu | Val | Tyr | Gln | |
| | | | 420 | | | | | 425 | | | | | 430 | | | |
| GCT | ATG | GAA | ACC | AAC | CAA | GTA | AAT | CCC | TTC | TCT | AAT | TTT | CTT | CAT | GTT | 1581 |
| Ala | Met | Glu | Thr | Asn | Gln | Val | Asn | Pro | Phe | Ser | Asn | Phe | Leu | His | Val | |
| | | 435 | | | | | 440 | | | | | 445 | | | | |
| GAC | CCT | AGA | AAA | TCC | AAC | TGAATGGTAT | CTCTTTGGCA | CGTTCAACTT | | | | | | | | 1629 |
| Asp | Pro | Arg | Lys | Ser | Asn | | | | | | | | | | | |
| | 450 | | | | | | | | | | | | | | | |

| | | | | |
|---|---|---|---|---|
| GGTCTCCTAT | TTTCAATAAC | TGTTGAAAAA | CATTTGTGTA | CACTTGTTGA CTCCAAGAAC | 1689 |
| TAAAAATAAT | GTGATTTCGC | CTCAATAAAT | GTAGTATTTC | ATTGAAAAGC AAAC | 1743 |

( 2 ) INFORMATION FOR SEQ ID NO:4:

( i ) SEQUENCE CHARACTERISTICS:
        ( A ) LENGTH: 454 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Pro | Glu | Phe | Leu | Glu | Asp | Pro | Ser | Val | Leu | Thr | Lys | Asp | Lys | Leu |
| 1 | | | | 5 | | | | 10 | | | | | 15 | | |
| Lys | Ser | Glu | Leu | Val | Ala | Asn | Asn | Val | Thr | Leu | Pro | Ala | Gly | Glu | Gln |
| | | | 20 | | | | | 25 | | | | 30 | | | |
| Arg | Lys | Asp | Val | Tyr | Val | Gln | Leu | Tyr | Leu | Gln | His | Leu | Thr | Ala | Arg |
| | | 35 | | | | | 40 | | | | | 45 | | | |
| Asn | Arg | Pro | Pro | Leu | Pro | Ala | Gly | Thr | Asn | Ser | Lys | Gly | Pro | Pro | Asp |
| | 50 | | | | | 55 | | | | | 60 | | | | |
| Phe | Ser | Ser | Asp | Glu | Glu | Arg | Glu | Pro | Thr | Pro | Val | Leu | Gly | Ser | Gly |
| 65 | | | | | 70 | | | | 75 | | | | | 80 | |
| Ala | Ala | Ala | Ala | Gly | Arg | Ser | Arg | Ala | Ala | Val | Gly | Arg | Lys | Ala | Thr |
| | | | | 85 | | | | | 90 | | | | | 95 | |
| Lys | Lys | Thr | Asp | Lys | Pro | Arg | Gln | Glu | Asp | Lys | Asp | Asp | Leu | Asp | Val |
| | | | 100 | | | | | 105 | | | | | 110 | | |
| Thr | Glu | Leu | Thr | Asn | Glu | Asp | Leu | Leu | Asp | Gln | Leu | Val | Lys | Tyr | Gly |
| | | | 115 | | | | | 120 | | | | | 125 | | |
| Val | Asn | Pro | Gly | Pro | Ile | Val | Gly | Thr | Thr | Arg | Lys | Leu | Tyr | Glu | Lys |
| | | 130 | | | | | 135 | | | | | 140 | | | |

| | | | | | | | | | | | | | | |
|---|---|---|---|---|---|---|---|---|---|---|---|---|---|---|
| Lys 145 | Leu | Leu | Lys | Leu | Arg 150 | Glu | Gln | Gly | Thr | Glu 155 | Ser | Arg | Ser | Ser | Thr 160 |
| Pro | Leu | Pro | Thr | Ile 165 | Ser | Ser | Ser | Ala | Glu 170 | Asn | Thr | Arg | Gln | Asn 175 | Gly |
| Ser | Asn | Asp | Ser 180 | Asp | Arg | Tyr | Ser | Asp 185 | Asn | Glu | Glu | Asp | Ser 190 | Lys | Ile |
| Glu | Leu | Lys 195 | Leu | Glu | Lys | Arg | Glu 200 | Pro | Leu | Lys | Gly | Arg 205 | Ala | Lys | Thr |
| Pro | Val 210 | Thr | Leu | Lys | Gln | Arg 215 | Arg | Val | Glu | His | Asn 220 | Gln | Ser | Tyr | Ser |
| Gln 225 | Ala | Gly | Ile | Thr | Glu 230 | Thr | Glu | Trp | Thr | Ser 235 | Gly | Ser | Ser | Lys | Gly 240 |
| Gly | Pro | Leu | Gln | Ala 245 | Leu | Thr | Arg | Glu | Ser 250 | Thr | Arg | Gly | Ser | Arg 255 | Arg |
| Thr | Pro | Arg | Lys 260 | Arg | Val | Glu | Thr | Ser 265 | Glu | His | Phe | Arg | Ile 270 | Asp | Gly |
| Pro | Val | Ile 275 | Ser | Glu | Ser | Thr | Pro 280 | Ile | Ala | Glu | Thr | Ile 285 | Met | Ala | Ser |
| Ser | Asn 290 | Glu | Ser | Leu | Val | Val 295 | Asn | Arg | Val | Thr | Gly 300 | Asn | Phe | Lys | His |
| Ala 305 | Ser | Pro | Ile | Leu | Pro 310 | Ile | Thr | Glu | Phe | Ser 315 | Asp | Ile | Pro | Arg | Arg 320 |
| Ala | Pro | Lys | Lys | Pro 325 | Leu | Thr | Arg | Ala | Glu 330 | Val | Gly | Glu | Lys | Thr 335 | Glu |
| Glu | Arg | Arg | Val 340 | Glu | Arg | Asp | Ile | Leu 345 | Lys | Glu | Met | Phe | Pro 350 | Tyr | Glu |
| Ala | Ser | Thr 355 | Pro | Thr | Gly | Ile | Ser 360 | Ala | Ser | Cys | Arg | Arg 365 | Pro | Ile | Lys |
| Gly | Ala 370 | Ala | Gly | Arg | Pro | Leu 375 | Glu | Leu | Ser | Asp | Phe 380 | Arg | Met | Glu | Glu |
| Ser 385 | Phe | Ser | Ser | Lys | Tyr 390 | Val | Pro | Lys | Tyr | Val 395 | Pro | Leu | Ala | Asp | Val 400 |
| Lys | Ser | Glu | Lys | Thr 405 | Lys | Lys | Gly | Arg | Ser 410 | Ile | Pro | Val | Trp | Ile 415 | Lys |
| Ile | Leu | Leu | Phe 420 | Val | Val | Val | Ala | Val 425 | Phe | Leu | Phe | Leu | Val 430 | Tyr | Gln |
| Ala | Met | Glu 435 | Thr | Asn | Gln | Val | Asn 440 | Pro | Phe | Ser | Asn | Phe 445 | Leu | His | Val |
| Asp | Pro | Arg | Lys 450 | Ser | Asn | | | | | | | | | | |

( 2 ) INFORMATION FOR SEQ ID NO:5:

( i ) SEQUENCE CHARACTERISTICS:
        ( A ) LENGTH: 2392 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 241..1275

( x i ) SEQUENCE DESCRIPTION: SEQ ID NO:5:

```
CCCTGCTACC AAGGCCCAGC TATGGCCCCA GGGTTGAAAA GTTATGAGGG TCAGGGGTCT      60
```

-continued

| | | | | | |
|---|---|---|---|---|---|
| TTTGTGTCCG | GGTCTGGCTT | GGCTTTGTGT | CCGCGAGTTT | TTGTTCCGCT | CCGCAGCGCT | 120
| CTTCCCGGGC | AGGAGCCGTG | AGGCTCGGAG | GCGGCAGCGC | GGTCCCCGGC | CAGGAGCAAG | 180
| CGCGCCGGCG | TGAGCGGCGG | CGGCAAAGGC | TGTGGGGAGG | GGGCTTCGCA | GATCCCCGAG | 240
| ATGCCGGAGT | TCCTGGAAGA | CCCCTCGGTC | CTGACAAAAG | ACAAGTTGAA | GAGTGAGTTG | 300
| GTCGCCAACA | ATGTGACGCT | GCCGGCCGGG | GAGCAGCGCA | AGACGTGTA | CGTCCAGCTC | 360
| TACCTGCAGC | ACCTCACGGC | TCGCAACCGG | CCGCCGCTCC | CCGCCGGCAC | CAACAGCAAG | 420
| GGCCCCCGG | ACTTCTCCAG | TGACAAGAG | CGCGAGCCCA | CCCCGGTCCT | CGGCTCTGGG | 480
| GCCGCCGCCG | CGGGCCGGAG | CCGAGCAGCC | GTCGGCAGGA | AAGCCACAAA | AAAAACTGAT | 540
| AAACCCAGAC | AAGAAGATAA | AGATGATCTA | GATGTAACAG | AGCTCACTAA | TGAAGATCTT | 600
| TTGGATCAGC | TTGTGAAATA | CGGAGTGAAT | CCTGGTCCTA | TTGTGGGAAC | AACCAGGAAG | 660
| CTATATGAGA | AAAAGCTTTT | GAACTGAGG | GAACAAGGAA | CAGAATCAAG | ATCTTCTACT | 720
| CCTCTGCCAA | CAATTTCTTC | TTCAGCAGAA | AATACAAGGC | AGAATGGAAG | TAATGATTCT | 780
| GACAGATACA | GTGACAATGA | AGAAGACTCT | AAAATAGAGC | TYAAGCTTGA | GAAGAGAGAA | 840
| CCACTAAAGG | GCAGAGCAAA | GACTCCAGTA | ACACTCAAGC | AAAGAAGAGT | TGAGCACAAT | 900
| CAGGTGGGAG | AAAAAACAGA | GGAAAGAAGA | GTAGAAAGGG | ATATTCTTAA | GGAAATGTTC | 960
| CCCTATGAAG | CATCTACACC | AACAGGAATT | AGTGCTAGTT | GCCGCAGACC | AATCAAAGGG | 1020
| GCTGCAGGCC | GGCCATTAGA | ACTCAGTGAT | TTCAGGATGG | AGGAGTCTTT | TTCATCTAAA | 1080
| TATGTTCCTA | AGTATGTTCC | CTTGGCAGAT | GTCAAGTCAG | AAAAGACAAA | AAAGGGACGC | 1140
| TCCATTCCCG | TATGGATAAA | AATTTTGCTG | TTTGTTGTTG | TGGCAGTTTT | TTTGTTTTTG | 1200
| GTCTATCAAG | CTATGGAAAC | CAACCAAGTA | AATCCCTTCT | CTAATTTTCT | TCATGTTGAC | 1260
| CCTAGAAAAT | CCAACTGAAT | GGTATCTCTT | TGGCACGTTC | AACTTGGTCT | CCTATTTTCA | 1320
| ATAACTGTTG | AAAAACATTT | GTGTACACTT | GTTGACTCCA | AGAACTAAAA | ATAATGTGAT | 1380
| TTCGCCTCAA | TAAATGTAGT | ATTTCATTGA | AAAGCAAACA | AAATATATAT | AAATGGACTT | 1440
| CATTAAAATG | TTTTGAACT | TTGGACTAGT | AGGAGATCAC | TTTGTGCCAT | ATGAATAATC | 1500
| TTTTTAGCT | CTGGAACTTT | TTGTAGGCTT | TATTTTTTA | ATGTGGGCAT | CTTATTTCAT | 1560
| TTTGAAAAA | ATGTATATGT | TTTTGTGTA | TTTGGGAAAC | GAAGGGTGAA | ACATGGTAGT | 1620
| ATAATGTGAA | GCTACACATT | TAAATACTTA | GAATTCTTAC | AGAAAGATT | TTAAGAATTA | 1680
| TTCTCTGCTG | AATAAAAACT | GCAAATATGT | GAAACATAAT | GAAATTCAGT | AAGAGGAAAA | 1740
| GTAACTTGGT | TGTACTTTTT | GTAACTGCAA | CAAAGTTTGA | TGGTGTTTAT | GAGGAAAAGT | 1800
| ACAGCAATAA | TCTCTTCTGT | AACCTTTATT | AATAGTAATG | TTGTTGTAGC | CCTATCATAC | 1860
| TCACTTTTTA | AGACACAGTA | TCATGAAAGT | CCTATTTCAG | TAAGACCCAT | TTACATACAG | 1920
| TAGATTTTTA | GCAGAGATCT | TTTAGTGTAA | CATACATATT | TTAGAGAATT | GTTGGCTAGC | 1980
| TGTACATGTT | TTGAAAAGCT | GTTTAGCTAG | CTATAAGGCT | ATAATTGGAA | ATTTGTATTT | 2040
| TTTATTTACA | GCAAAACATT | TATTCAGTCA | TCCAGTTTGC | TACCAAAATA | TGTTTTAGAT | 2100
| AAGTGTGTGT | ATGTTTGTTT | AGAAGTTAGA | AATTGTAAAC | ACTGGTCTTA | TGTTTCATTT | 2160
| GGATTCATTA | TTGCATTGTC | TTGTTACCAG | AAACAAATTT | TGCCGAGCTT | TTTTTGCCCT | 2220
| ATATTTCCCA | GCATAATTTG | ATTAGAAAGT | ACAAAAGGG | CCGGGCGCGG | TGGCTTACGC | 2280
| CTGTAATCCC | AGCACTTTGG | GAGGCCAGGG | CGGGTGGATC | ACGAGGTCAG | GAGATCGGGA | 2340
| CCATCCTGGC | CAACATGGTG | AAACCCCGTC | TCTACTAAAA | AAAAAAAAA | AA | 2392

( 2 ) INFORMATION FOR SEQ ID NO:6:

( i ) SEQUENCE CHARACTERISTICS:
  ( A ) LENGTH: 345 amino acids
  ( B ) TYPE: amino acid
  ( D ) TOPOLOGY: unknown ( i i ) MOLECULE TYPE: peptide ( x i ) SEQUENCE DESCRIPTION: SEQ ID NO:6:

```
Met Pro Glu Phe Leu Glu Asp Pro Ser Val Leu Thr Lys Asp Lys Leu
 1               5                  10                  15

Lys Ser Glu Leu Val Ala Asn Asn Val Thr Leu Pro Ala Gly Glu Gln
            20                  25                  30

Arg Lys Asp Val Tyr Val Gln Leu Tyr Leu Gln His Leu Thr Ala Arg
        35                  40                  45

Asn Arg Pro Pro Leu Pro Ala Gly Thr Asn Ser Lys Gly Pro Pro Asp
    50                  55                  60

Phe Ser Ser Asp Glu Glu Arg Glu Pro Thr Pro Val Leu Gly Ser Gly
65                  70                  75                  80

Ala Ala Ala Ala Gly Arg Ser Arg Ala Ala Val Gly Arg Lys Ala Thr
                85                  90                  95

Lys Lys Thr Asp Lys Pro Arg Gln Glu Asp Lys Asp Asp Leu Asp Val
            100                 105                 110

Thr Glu Leu Thr Asn Glu Asp Leu Leu Asp Gln Leu Val Lys Tyr Gly
            115                 120                 125

Val Asn Pro Gly Pro Ile Val Gly Thr Thr Arg Lys Leu Tyr Glu Lys
    130                 135                 140

Lys Leu Leu Lys Leu Arg Glu Gln Gly Thr Glu Ser Arg Ser Ser Thr
145                 150                 155                 160

Pro Leu Pro Thr Ile Ser Ser Ser Ala Glu Asn Thr Arg Gln Asn Gly
                165                 170                 175

Ser Asn Asp Ser Asp Arg Tyr Ser Asp Asn Glu Glu Asp Ser Lys Ile
            180                 185                 190

Glu Leu Lys Leu Glu Lys Arg Glu Pro Leu Lys Gly Arg Ala Lys Thr
            195                 200                 205

Pro Val Thr Leu Lys Gln Arg Arg Val Glu His Asn Gln Val Gly Glu
    210                 215                 220

Lys Thr Glu Glu Arg Arg Val Glu Arg Asp Ile Leu Lys Glu Met Phe
225                 230                 235                 240

Pro Tyr Glu Ala Ser Thr Pro Thr Gly Ile Ser Ala Ser Cys Arg Arg
                245                 250                 255

Pro Ile Lys Gly Ala Ala Gly Arg Pro Leu Glu Leu Ser Asp Phe Arg
            260                 265                 270

Met Glu Glu Ser Phe Ser Ser Lys Tyr Val Pro Lys Tyr Val Pro Leu
            275                 280                 285

Ala Asp Val Lys Ser Glu Lys Thr Lys Lys Gly Arg Ser Ile Pro Val
    290                 295                 300

Trp Ile Lys Ile Leu Leu Phe Val Val Val Ala Val Phe Leu Phe Leu
305                 310                 315                 320

Val Tyr Gln Ala Met Glu Thr Asn Gln Val Asn Pro Phe Ser Asn Phe
                325                 330                 335

Leu His Val Asp Pro Arg Lys Ser Asn
            340                 345
```

( 2 ) INFORMATION FOR SEQ ID NO:7:

( i ) SEQUENCE CHARACTERISTICS:
    ( A ) LENGTH: 5 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:7:

```
Arg  Lys  Asp  Val  Tyr
 1                    5
```

( 2 ) INFORMATION FOR SEQ ID NO:8:

( i ) SEQUENCE CHARACTERISTICS:
    ( A ) LENGTH: 95 base pairs
    ( B ) TYPE: nucleic acid
    ( C ) STRANDEDNESS: unknown
    ( D ) TOPOLOGY: unknown ( i i ) MOLECULE TYPE: cDNA ( x i ) SEQUENCE DESCRIPTION: SEQ ID NO:8:

```
GGGAATTCGC  CGCCGAGATG  CCGGAGTTCC  TGGAAGACCC  CTCGGTCCTG  ACGAAAGAGA        60
AGTTGAAGAG  TGAGTTGGTC  GCCAACAATG  TGACG                                    95
```

( 2 ) INFORMATION FOR SEQ ID NO:9:

( i ) SEQUENCE CHARACTERISTICS:
    ( A ) LENGTH: 95 base pairs
    ( B ) TYPE: nucleic acid
    ( C ) STRANDEDNESS: unknown
    ( D ) TOPOLOGY: unknown ( i i ) MOLECULE TYPE: cDNA ( x i ) SEQUENCE DESCRIPTION: SEQ ID NO:9:

```
GGGAATTCAG  CGCTTCAGGG  CCGTCAGGTG  CTGCAGGTAG  AGCTGCACAT  ACACGTCTTT        60
GCGCTGCTCC  CCGGCCGGGA  GCGTCACATT  GTTGG                                    95
```

( 2 ) INFORMATION FOR SEQ ID NO:10:

( i ) SEQUENCE CHARACTERISTICS:
    ( A ) LENGTH: 45 base pairs
    ( B ) TYPE: nucleic acid
    ( C ) STRANDEDNESS: unknown
    ( D ) TOPOLOGY: unknown ( i i ) MOLECULE TYPE: cDNA ( x i ) SEQUENCE DESCRIPTION: SEQ ID NO:10:

```
TCTATCAAGC  TATGGAAACC  AACCAAGTAA  ATCCCTTCTC  TAATT                        45
```

( 2 ) INFORMATION FOR SEQ ID NO:11:

( i ) SEQUENCE CHARACTERISTICS:
    ( A ) LENGTH: 50 base pairs
    ( B ) TYPE: nucleic acid
    ( C ) STRANDEDNESS: unknown
    ( D ) TOPOLOGY: unknown ( i i ) MOLECULE TYPE: cDNA ( x i ) SEQUENCE DESCRIPTION: SEQ ID NO:11:

```
CATTCAGTTG  GATTTTCTAG  GGTCAACATG  AAGAGAATTA  GAGAAGGGAT                   50
```

RECOMBINANT HUMAN THYMOPOIETIN PROTEINS AND USES THEREFOR

FIELD OF THE INVENTION

The present invention relates generally to human thymopoietin proteins and their use in diagnosis and therapy of various immune and nervous system conditions.

BACKGROUND OF THE INVENTION

Thymopoietin is a polypeptide produced by cells of the thymus and other cells, which has been implicated in various immune and nervous system pathways. There have been several attempts to isolate and sequence various species of thymopoietin. Thymopoietin was originally isolated as a 5 kDa, 49 amino acid protein from bovine thymus [Goldstein et al, *Nature*, 247:11–14 (1974). See also, Schlesinger and Goldstein, *Cell*, 5:361–365 (1975).] Later work described by T. Audhya et al, *Biochemistry*, 20(21):6195–6200 (1981) purported to provide the complete sequences for bovine thymopoietins. Three 49 amino acid sequences were described therein. Zevin-Sonkin et al, *Immunol. Lett.*, 31:301–310 (1992) report the isolation of a bovine cDNA using oligonucleotide probes based on the original 49 amino acid bovine TP protein sequence [Schlesinger and Goldstein, cited above], which encodes the originally determined sequence at the N-terminus of a larger open reading frame.

The active site of thymopoietin, a pentapeptide of the sequence Arg-Lys-Asp-Val-Tyr [SEQ ID NO:7], was described by G. Goldstein et al, *Science*, 204:1309–1310 (1979) and in U.S. Pat. No. 4,190,646. There is a wealth of art describing analogs of the active site, termed thymopentin and their uses.

Attempts to isolate and sequence thymopoietin continue. For example, European Patent Application 502,607 describes bovine thymopoietin or thymopoietin-like cDNA clones.

Despite these publications and the knowledge of thymopoietin, to date, the cloning of the complete human thymopoietin gene and its recombinant expression has not been described. There remains a need in the art for a convenient method of producing human thymopoietin, fragments thereof, and polynucleotide sequences encoding the protein.

SUMMARY OF THE INVENTION

In one aspect, the invention provides three novel polynucleotide sequences encoding human thymopoietin proteins referred to as α, β and γ, isolated from other cellular materials with which they are naturally associated, and having a biological activity associated with immune function. These polynucleotide sequences are illustrated in FIG. 1 [SEQ ID NO:1], FIG. 2 [SEQ ID NO:3] and FIG. 3 [SEQ ID NO:5]. Fragments of these sequences are also embodied by this invention. These sequences or fragments thereof may also be optionally associated with conventionally used labels for diagnostic or research use.

In another aspect, the invention provides an expression vector which contains at least a polynucleotide sequence described above. In still another aspect, a host cell transformed with such an expression vector is provided.

In still another aspect, the present invention provides a method for producing a recombinant human thymopoietin protein which involves transforming a host cell with an expression vector containing a recombinant polynucleotide encoding a human thymopoietin protein by incubating the host cell and expression vector, and following transformation, culturing the transformed host cell under conditions that allow expression of the human thymopoietin.

In still another aspect, the present invention provides three proteins characterized by having activity in the immune system. These proteins are illustrated in FIGS. 1–3, and are designated herein as α SEQ ID NO: 2, β SEQ ID NO: 4, and γ SEQ ID NO: 6, respectively. These proteins are characterized by being isolated from the cellular material with which they are naturally associated. Advantageously, one or more of these sequences is capable of being produced recombinantly.

In yet another aspect, the present invention provides a pharmaceutical composition containing at least one of the thymopoietin proteins α, β or γ, and a pharmaceutically acceptable carrier.

In another aspect, the invention provides a method of treating a subject with a disorder of the immune or nervous system by administering to the subject a pharmaceutical composition of the invention.

In yet a further aspect, the invention provides a diagnostic reagent, such as a polyclonal or monoclonal antibody generated by use of one of these thymopoietin proteins or fragments thereof.

In another aspect, the invention provides a diagnostic reagent, such as a DNA probe, i.e., an oligonucleotide fragment derived from the polynucleotide sequence encoding one of the proteins of the invention or from the complementary strand. The reagents may be optionally associated with a detectable label.

Other aspects and advantages of the present invention are described further in the following detailed description of the preferred embodiments thereof.

BRIEF DESCRIPTION OF THE DRAWINGS

FIGS. 1A through 1D consecutively illustrate the nucleic acid [SEQ ID NO:1] and amino acid [SEQ ID NO:2] sequences of human thymopoietin α.

FIGS. 2A through 2C consecutively illustrate the nucleic acid [SEQ ID NO:3] and amino acid [SEQ ID NO:4] sequences of human thymopoietin β.

FIGS. 3A through 3C consecutively illustrate the nucleic acid [SEQ ID NO:5] and amino acid [SEQ ID NO:6] sequences of human thymopoietin γ.

DETAILED DESCRIPTION OF THE INVENTION

The present invention provides novel recombinant human thymopoietin (rhTP) nucleic acid sequences and proteins, designated α, β, and γ. These sequences are provided in FIGS. 1–3 [SEQ ID NO: 1–6], respectively. Advantageously, the nucleic acid sequences are useful as diagnostic probes, in gene therapy, and in the production of thymopoietin proteins. The proteins are useful for a variety of therapeutic and diagnostic applications, as well as for generation of other therapeutic and diagnostic reagents.

In the figures, the sequences are numbered differently than in the Sequence Listing. Specifically, in the figures, the sequences have been numbered so that amino acid +1 is the amino terminal proline of mature TP and nucleotide +1 is the first nucleotide of the proline codon. The initial Met, its codon, and the 5' end of the sequences all are designated in negative numbers. This is indicative of the fact that the initiating methionine is removed co-translationally by methionine aminopeptidase [R. A. Bradshaw, *Trends Biochem. Sci.*, 14:276–279 (1989)]. In contrast, due to the limitations of the PatentIn program, the Sequence Listing does not contain any negative numbers. Thus, in the Sequence Listing, the 5' non-coding region begins with positive numbers and the first amino acid is Met. Throughout this application, fragments of the sequences will be referred to as in the figures, with the numbers of the Sequence Listing following in brackets.

Figure 4A:
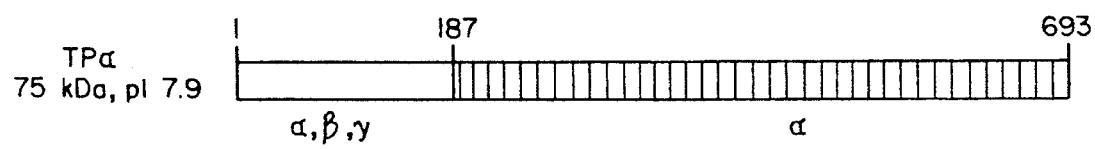
FIG. 4A provides a schematic diagram of the protein sequence of thymopoietin protein α.
Figure 4B:
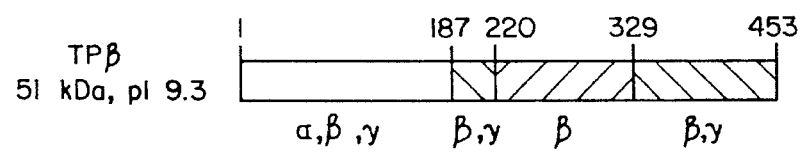
FIG. 4B provides a schematic diagram of the protein sequence of thymopoietin protein β.
Figure 4C:
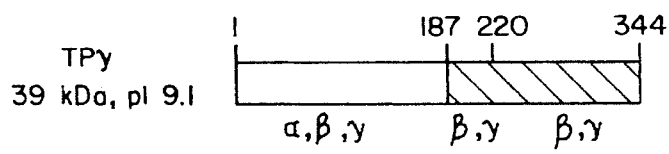
FIG. 4C provides a schematic diagram of the protein sequence of thymopoietin protein γ.

As used herein, the term "β numbering system" reflects the fact that two common regions are shared by hTPβ and hTPγ and are identified by reference to the amino acids of the hTPβ protein. Because hTPβ has a 109 amino acid insert (indicated in bold in FIG. 2), discussed in detail below, between amino acids 220 and 221 of hTPγ, in the β-numbering system, amino acid 330 of hTPβ is equivalent to amino acid 221 of hTPγ (subtraction of the 109 β-specific amino acids results in correct numbering for γ). See FIGS. 4B and 4C.

The present invention provides the human thymopoietin α, β, and γ proteins. These proteins are characterized by the amino acid sequences of FIG. 1–3, respectively. Human TPα is 693 amino acids in length [SEQ ID NO:2] having a molecular weight of 75 kDa, hTPβ is a 453 amino acid protein [SEQ ID NO:4] having a molecular weight of 51 kDa; and human TPγ is a 344 amino acid protein [SEQ ID NO:6] having a molecular weight of 39 kDa.

TPs α, β, and γ have identical N-terminal domains through $Glu_{187}$ (indicated by an * in FIGS. 1–3). This region is termed αβγ [amino acids 2–188 of SEQ ID NO: 2, 4,6]. See FIGS. 4A–4C. After $Glu_{187}$, TP α [SEQ ID NO:2] diverges from TPs β [SEQ ID NO:4] and γ [SEQ ID NO:6]. This unique region from amino acid 188 through amino acid 693 of hTPα [189–694 SEQ ID NO:2] is termed simply α. A unique hTPβ region is found at amino acid 221 through amino acid 329 [222–330 of SEQ ID NO:4]. TPγ differs from TPβ only in missing the β-specific domain containing amino acids 221–329 of TPβ (222–330 of SEQ ID NO:4]. The two regions common to hTP β and hTP γ are from amino acid 188–220 (βγ1) [189–221 SEQ ID NO:4] and from amino acid 330–453 (βγ2) [331–454 SEQ ID NO: 4], using the β numbering system. In regions where the amino acid sequences of TPs α [SEQ ID NO:2], β [SEQ ID NO:4], and γ [SEQ ID NO:6] are identical, their nucleotide sequences are identical as well, consistent with their originating via alternative splicing of transcripts from a single gene. This was confirmed by sequencing of genomic clones.

Included in this invention are fragments of the TP α, β and γ proteins [SEQ ID NOS: 2, 4, 6]. Preferably, these fragments are at least about 3 amino acids in length and are characterized by being biologically active. These fragments are desirable for use in generating therapeutic or diagnostic antibodies or for other diagnostic purposes. Particularly desirable are the following fragments which have been found to be immunogenic sites. The following Table I makes use of the nomenclature above, e.g. αβγ $hTP_{1-52}$ relates to amino acids 1–52 of α, β and γ (amino acids 2–53 of SEQ ID NO: 2, 4 and 6).

TABLE I

| Peptides | SEQ ID NOS: | Peptides | SEQ ID NOS: |
|---|---|---|---|
| αβγ $hTP_{1-52}$ (2–53) | 2, 4, 6 | α $hTP_{425-443}$ (426–444) | 2 |
| αβγ $hTP_{1-19}$ (2–20) | 2, 4, 6 | α $hTP_{518-538}$ (519–539) | 2 |
| αβγ $hTP_{28-39}$ (29–40) | 2, 4, 6 | α $hTP_{604-622}$ (605–623) | 2 |
| αβγ $hTP_{40-52}$ (41–53) | 2, 4, 6 | α $hTP_{188-197}$ (189–198) | 2 |
| αβγ $hTP_{29-50}$ (30–51) | 2, 4, 6 | α $hTP_{188-202}$ (189–203) | 2 |
| αβγ $hTP_{56-71}$ (57–72) | 2, 4, 6 | βγ1 $hTP_{196-215}$ (197–216) | 4, 6 |
| αβγ $hTP_{92-108}$ (93–109) | 2, 4, 6 | β $hTP_{247-265}$ (248–266) | 4 |
| αβγ $hTP_{168-187}$ (169–188) | 2, 4, 6 | β $hTP_{312-329}$ (313–330) | 4 |
| α $hTP_{233-253}$ (234–254) | 2 | βγ2 $hTP_{332-348}$ (333–349) | 4, 6 |
| α $hTP_{342-362}$ (343–363) | 2 | βγ2 $hTP_{397-412}$ (398–413) | 4, 6 |

Also included in the invention are analogs of the α, β, and γ proteins provided herein. Typically, such analogs differ by only 1, 2, 3 or 4 codon changes. Examples include polypeptides with minor amino acid variations from the illustrated amino acid sequences of α, β or γ (FIGS. 1–3; SEQ ID NOS: 2, 4, 6); in particular, conservative amino acid replacements. Conservative replacements are those that take place within a family of amino acids that are related in their side chains and chemical properties.

Additionally, the α, β, and γ proteins [SEQ ID NOS: 2, 4, 6] of the invention may be altered, for example to improve production or to confer some other desired property upon the protein. For example, the transmembrane region of the protein, identified herein, may be removed, fully or in part, to obtain a soluble form of the protein. Alternatively, a TP protein of the invention may be truncated or modified to prevent localization to the nucleus or into the nuclear membrane. For example, the TPα may be modified to remove the putative nucleus localization motif at amino acids 189–195 [aa 190–196 of SEQ ID NO:2]. The carboxy terminal transmembrane localization motifs of TPβ and TPγ can also be removed, e.g., at aa 411–431 [aa412–432 of SEQ ID NO: 4] (indicated by double underlining in FIGS. 2 and 3).

Without being bound by the theory of the mechanism by which these rhTP proteins function, the inventors believe that each protein has unique characteristics. Each of the proteins plays a role in cellular physiology, especially in the immune system. As illustrated in the Examples below, TP mRNA expression was detected in all tissues examined, suggesting that some TP function(s) may be important in many or all cell types. However, TP mRNA expression was highest in adult thymus and in fetal liver, a major fetal site for production of T cell precursors. This suggests that TPs may play important roles in T cell development and function.

Human TPs α, β, and γ [SEQ ID NOS: 2, 4, 6] do not appear to contain a cleavable hydrophobic amino-terminal signal peptide for directing the nascent peptide into the ER/Golgi pathway for protein secretion. The apparent absence of classical N-terminal hydrophobic cleavable signal sequences for secretion in TP α, β, and γ suggests that the proteins [SEQ ID NOS: 2, 4, 6] may be largely localized intracellularly and may have important intracellular functions. However, preliminary analysis of conditioned media from human and mouse T-cell lines using a TP immunoassay is consistent with the presence of one or more forms of extracellular TP. Extracellular TP may be generated by an alternative secretion pathway such as that used by interleukin-1 or the fibroblast growth factors, which also have no classical signal sequences [A. Rubartelli et al, *Biochem. Soc. Trans.*, 19:255–259 (1991)].

TPs β and γ [SEQ ID NOS: 4 and 6] contain a hydrophobic domain near their carboxy termini, which may be a transmembrane signal-anchor domain. This putative transmembrane region is found at amino acid sequences 410–430, using the β numbering system [411–431 of SEQ ID NO:4]. In contrast, TP α [SEQ ID NO: 2] does not appear to contain a membrane-spanning domain and is expected to be a soluble protein. Preliminary analysis of subcellular localization by immunofluorescence microscopy confirms the localizations suggested above, i.e., TPB and TPγ being localized to the nuclear membrane and TPα being localized within the nucleus.

Examination of TP α, β, and γ sequences [SEQ ID NOS: 2, 4, 6] for additional motifs revealed potential phosphorylation sites for several protein kinases. Of particular interest is a consensus sequence for tyrosine phosphorylation in TPα [SEQ ID NO: 2] at $Tyr_{626}$ (indicated by underlining in FIG. 1). Typically, phosphorylation on tyrosine serves to regulate activities of many proteins, particularly proteins involved in controlling cell growth and differentiation.

The nucleic acid sequences encoding these proteins are themselves useful for a variety of diagnostic and therapeutic uses, including gene therapy. Thus, the present invention also provides the nucleic acid sequences encoding hTPα, β and γ [SEQ ID NOS: 2, 4, 6] and fragments thereof. The nucleic acid sequences of the invention are characterized by the DNA sequences of FIG. 1–3 [SEQ ID NOS: 1, 3, 5], respectively. Note that the first approximately 53 nucleotides of the TPγ sequence of FIG. 3 may either be an alternatively spliced original TPγ sequence, or alternatively may represent a non-TP cloning artifact.

In addition to the fragments encoding the peptide sequences of Table I, other fragments of these sequences may prove useful for a variety of uses. Desirably, these fragments are at least about 15 nucleotides in length and encode a desired amino acid sequence, e.g. an epitope, a therapeutically useful peptide, or the like. These nucleotide sequences of the invention may be isolated as in Example 1, described below. Alternatively, these sequences may be constructed using conventional genetic engineering or chemical synthesis techniques.

According to the invention, the nucleic acid sequences [SEQ ID NOS: 1, 3, 5] coding for, as well as the encoded α, β, and γ proteins [SEQ ID NOS: 2, 4, 6] described above and provided in FIGS. 1–3, may be modified. Utilizing the sequence data in these figures, it is within the skill of the art to obtain other polynucleotide sequences encoding the proteins of the invention. Such modifications at the nucleic acid level include, for example, modifications to the nucleotide sequences which are silent or which change the amino acids, e.g. to improve expression or secretion. Alternatively, the amino acid sequence may be modified to enhance protein stability or other characteristics, e.g. binding activity or bioavailability. In still another alternative, the polynucleotide and/or protein sequences may be modified by adding readily assayable tags to facilitate quantitation, where desirable. Nucleotides may be substituted, inserted, or deleted by known techniques, including, for example, in vitro mutagenesis and primer repair. Also included are allelic variations, caused by the natural degeneracy of the genetic code. For example, in one of the hTPα cDNA clones isolated, nucleotide 1792 is a G, which changes amino acid 598 from Gln to Glu (compare to SEQ ID NO:1 in which nucleotide 1792 is a C). Note, also, nucleotide 579 is C in the β clone λT.6 and in a genomic clone, but T in the sequenced subclone of λ clone λT.206, in both cases encoding leucine.

In addition to isolated nucleic acid sequences [SEQ ID NOS: 1, 3, 5] encoding the thymopoietin proteins α, β, and γ [SEQ ID NOS: 2, 4, 6] described herein, this invention also encompasses other nucleic acid sequences, such as those complementary to the illustrated DNA sequences. Useful DNA sequences also include those sequences which hybridize under high or moderately high stringency conditions [see, T. Maniatis et al, *Molecular cloning (A Laboratory Manual)*, Cold Spring Harbor Laboratory (1982), pages 387 to 389] to the DNA sequences illustrated in FIG. 1–3. An example of a highly stringent hybridization condition is hybridization at 4XSSC at 65° C. followed by a washing in 0.1XSSC at 65° C. for an hour. Alternatively, an exemplary highly stringent hybridization condition is in 50% formamide, 4XSSC at 42° C. Other, moderately high stringency conditions may also prove useful, e.g. hybridization in 4XSSC at 55° C., followed by washing in 0.1XSSC at 37° C. for an hour. Alternatively, an exemplary moderately high stringency hybridization condition is in 50% formamide, 4XSSC at 30° C.

Once constructed, or isolated, as described in further detail in Example 1 below, these DNA sequences or suitable fragments are preferably employed to obtain proteins of this invention.

The DNA sequences of the invention are inserted into a suitable expression system to obtain the proteins of the invention. Desirably, the polynucleotide sequence is operably linked to a heterologous expression control sequence permitting expression of the human thymopoietin protein. Numerous types of appropriate expression systems are known in the art for mammalian (including human) expression, as well as insect, yeast, fungal, and bacterial expression, by standard molecular biology techniques. Bacterial expression systems, using such host cells as *E. coli*, are desirable for expression of thymopoietin.

Mammalian cell expression vectors are also desirable for expression. The mammalian cell expression vectors described herein may be synthesized by techniques well known to those skilled in this art. The components of the vectors, e.g. replicons, selection genes, enhancers, promoters, and the like, may be obtained from natural sources or synthesized by known procedures.

The transformation of these vectors into appropriate host cells can result in expression of the selected thymopoietin proteins. Other appropriate expression vectors, of which numerous types are known in the art for mammalian expression, can also be used for this purpose.

Suitable cells or cell lines for this method are mammalian cells, such as Human 293 cells, Chinese hamster ovary cells (CHO), the monkey COS-1 cell line or murine 3T3 cells derived from Swiss, Balb-c or NIH mice. The selection of suitable mammalian host cells and methods for transformation, culture, amplification, screening, and product production and purification are known in the art. [See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446]. Another suitable mammalian cell line is the CV-1 cell line.

Similarly useful as host cells suitable for the present invention are bacterial cells. For example, the various strains of *E. coli* (e.g., HB101, MC1061, and strains used in the following examples) are well-known as host cells in the field of biotechnology. Various strains of *B. subtilis, Pseudomonas*, other bacilli and the like may also be employed in this method.

Many strains of yeast cells known to those skilled in the art are also available as host cells for expression of the polypeptides of the present invention. Additionally, where desired, insect cells may be utilized as host cells in the method of the present invention. [See, e.g. Miller et al, *Genetic Engineering,* 8:277–298 (Plenum Press 1986) and references cited therein]. Fungal cells may also be employed as expression systems.

The host cells transformed with the one or more vectors carrying the thymopoietin DNA, e.g. by conventional means, may then be cultured under suitable conditions to obtain expression of the desired protein. The method of this present invention therefore comprises culturing a suitable cell or cell line, which has been transformed with a DNA sequence coding for thymopoietin, the coding sequence under the control of a transcriptional regulatory sequence. The expressed protein is then recovered, isolated, and purified from the culture medium (or from the cell, if expressed intracellularly) by appropriate means known to one of skill in the art.

For example, the proteins may be isolated following cell lysis in soluble form, or extracted in guanidine chloride. For example, a currently preferred method for purification of hTPα [SEQ ID NO: 2] is by lysis of the *E. coli* by freezing and thawing followed by sonication, and extraction of the recombinant protein with solutions containing 20 mM Tris HCl, pH 7.6, 1M urea or 1M guanidine HCl. In addition, molecular sieving, e.g. using a 300 kDa sieve [BioRad TSK-250] column, may be used.

If desired, the TP proteins of the invention may be produced as a fusion protein. For example, it may be desirable to produce such TP fusion proteins, to enhance expression of the protein in a selected host cell, or to improve purification. Suitable fusion partners for the rhTP proteins of the invention are well known to those of skill in the art and include, among others, β-galactosidase and poly-histidine.

Other uses for the polynucleotide sequences of this invention include diagnostic and therapeutic uses. For example, the novel recombinant hTP nucleic acid sequences or genes of the invention, or suitable fragments thereof, are useful in gene therapy for correcting abnormalities, for example, those associated with an immune or nervous system disorder.

Another example involves incorporating a desired hTP nucleic acid sequence of the invention into a suitable vector or other delivery system. Suitable delivery systems are well known to those of skill in the art. Vectors containing such sequences may be administered, thus, treating deficiencies of TP via in vivo expression of the proteins of the invention. Such delivery systems enable the desired hTP gene to be incorporated into the target cell and to be translated by the cell. In such a manner, a recombinant hTP protein of the invention can be provided to a cell, particularly a cell in an individual having a condition characterized by a deficiency in TP.

These polynucleotide sequences of this invention may also be associated with detectable labels or components of label systems conventionally used in diagnostic or therapeutic methods. As diagnostic agents the polynucleotide sequences may be employed to detect or quantitate normal or mutant hTP mRNA or detect mutations in TP DNA in a patient sample.

The TPα, β and γ proteins [SEQ ID NOS: 2, 4, 6] of the invention and compositions containing these proteins demonstrate a variety of regulatory effects on the mammalian immune system. For example, peptides of this invention offer treatment therapies for chronic infection, autoimmune disorders, and certain affective psychiatric or neurological disorders, as well as other conditions characterized by a disorder of the immune system. Because of the immunomodulatory characteristics of the subject proteins, they are therapeutically useful in the treatment of humans, and possibly animals, since they are capable of effecting changes in the immune system of the mammal.

These proteins have therapeutic uses in humans. For example, the rhTP proteins in a pharmaceutical composition of the present invention may be administered in vivo to raise levels of circulating TP in an individual requiring same, e.g., a patient suffering from disorders, e.g., stress related to insufficient levels of circulating hTP. Alternatively, the rhTP proteins of the invention may be administered in such a way as to produce a localized response. It is anticipated that these rhTP proteins will have longer half-lives than thymopentin.

Also, the proteins according to the present invention may be used to diminish the effects of aging on the immune system. As the thymus shrinks with age, the level of thymopoietin decreases. Thus, administration of proteins of this invention which have biological activity similar to thymopoietin can help reduce the effects of aging related to inefficient or non-functioning immune systems.

The invention further provides pharmaceutical compositions and a method for treatment of conditions resulting from disorder of the immune system and/or nervous system of a subject, which comprises administering to said subject a therapeutically-effective amount of at least one of the proteins or pharmaceutical compositions of this invention. Such pharmaceutical compositions of the invention contain one or more of the above-described proteins or acid- or base-addition salts thereof. Optionally, such compositions may further contain conventional therapeutic or other agents useful in treating the immune or other disorder. The subject proteins or pharmaceutical compositions containing the proteins or their acid or basic salts are generally considered to be useful when cellular immunity is an issue and particularly when there are deficiencies in immunity. The pharmaceutical compositions of the invention are also useful in treating imbalances and dysfunctions in the central nervous system.

As used herein, the term "therapeutically-effective amount" means an amount which is effective to treat the conditions referred to above. A protein of the present invention is generally effective when parenterally administered in amounts above about 0.01 µg protein per kg of body weight (µg/kg), and preferably from about 1 µg/kg to about 10 mg/kg.

To prepare the pharmaceutical compositions of the present invention, a protein of this invention is combined as the active ingredient in intimate admixture with a pharmaceutical carrier according to conventional pharmaceutical compounding techniques. This carrier may take a wide variety of forms depending on the form of preparation desired for administration, e.g., sublingual, rectal, nasal, or parenteral. The presently preferred route of administration is parenteral.

For parenteral products the carrier will usually comprise sterile water, although other ingredients may be included, e.g., to aid solubility or for preservation purposes. Injectable suspensions may also be prepared, in which case appropriate liquid carriers, suspending agents, and the like may be employed.

Both the nucleic acid and amino acid sequences of the invention are useful for generating reagents for use in diagnostic assays. The nucleic acid sequences, or suitable fragments thereof, are also useful for detecting thymopoietin mRNA levels, and gene mutations. Further, antibodies, including monoclonal, polyclonal, and recombinant antibodies, may be generated to these peptide sequences which may similarly be useful for measuring thymopoietin levels. Such monoclonal antibodies may be generated using the standard Kohler and Milstein technique as well as well known modifications thereof. Alternatively, other known techniques for the generation of monoclonal or recombinant antibodies may be employed using fragments of the proteins or polynucleotide sequences of this invention to generate antibodies suitable for both therapeutic and diagnostic application.

Thus, the invention provides a method for diagnosing an immune or nervous system disorder, and/or detecting a condition associated with increased or decreased levels of thymopoietin using conventional diagnostic assay methods. Such a diagnostic method may be performed using a monoclonal or polyclonal antibody directed against an epitope of protein α, β, or γ, or a DNA probe of the invention, in an appropriate assay system.

The following examples illustrate the preferred methods for isolating and expressing the novel sequences of the invention. In view of the disclosure of these sequences, other methods for obtaining them are available to the art and are therefore encompassed in this invention. These examples are illustrative only and do not limit the scope of the invention.

EXAMPLE 1

Isolation of Human Thymopoietin cDNA Clones

Initial human thymopoietin cDNA clones were isolated from a commercial cDNA library prepared from human thymus RNA in the vector lambda GT10 (Clontech; Palo Alto, Calif.). The sequence of human thymopoietin α was determined from the overlapping cDNA clones λhTP-T.32 and λhTP-T.153, which together provide the complete open reading frame, and was verified in the genomic clone λSHG-1, obtained from a commercial genomic library in vector λFIXII [Stratagene]. Isolation of the clones from which the TP proteins α, β and γ of the invention were derived was performed as follows.

The library was probed using two 95-mer oligonucleotides containing a 14 nucleotide overlap based on the bovine thymopoietin sequence of Zevin-Sonkin et al, *Immunol. Lett.*, 31:301–310 (1992). The sense oligonucleotide sequence was: GGGAATTCGC CGCCGAGATG CCGGAGTTCC TGGAAGACCC CTCGGTCCTG ACGAAA GAGA AGTTGAAGAG TGAGTTGGTC GCCAACAATG TGACG :SEQ ID NO:8. The antisense oligonucleotide sequence was: GGGAATTCAG CGCTTCAGGG CCGT CAGGTG CTGCAGGTAG AGCTGCACAT ACACGTCTTT GCGCTGCTCC CCGGCCGGGA GCGT CACATT GTTGG: SEQ ID NO:9.

Clones λhTP-T.6 (hTPβ), λhTP-T.17 (hTPβ), and λhTP-T.32 (hTPα) were among the clones isolated in this initial screen. Clone λhTP-T.153 (hTPα) was among the clones isolated in a subsequent screen in which the probe was a 0.3 kb fragment isolated from the 3' end of λhTP-T.32 by digestion with the restriction enzymes Bam HI and Eco RI. Clones λhTP-T.206 (hTPγ) and λhTP-T.209 (hTPβ) were among the clones isolated in a screen in which the probe was two overlapping oligonucleotides derived from the 3' end of λhTP-T.17, the sense oligonucleotide being SEQ ID NO:10 :TCTATCAAGC TATGGAAACC AACCAAGTAA ATC- CCTTCTC TAATT and the antisense oligonucleotide being SEQ ID NO: 11: CATTCAGTTG GATTTTCTAG GGT- CAACATG AAGAGAATTA GAGAAGGGAT.

The sequence of human thymopoietin γ was determined from clone λhTP-T.206. The sequence of human thymopoietin β was determined from the overlapping clones λhTP-T.6, λhTP-T.17, and λhTP-T.209. The clone numbers are based solely on the order of isolation from the library.

EXAMPLE 2

Analysis of TP Clones

Sequences were determined using Sequenase Version 2.0 (United States Biochemical) or Taq polymerase (Perkin-Elmer), on the original clone DNA, or on fragments subcloned into plasmid vectors. All sequences reported here were determined on both strands of at least one clone, and, except for the 3' untranslated sequences of TPs β and γ, have been confirmed in one or more additional clones.

The sequences of human TP α, β and γ are similar but not identical to the bovine sequence of Zevin-Sonkin et al, cited above, between amino acids 1–81, but show no further similarity beyond this point. Sequencing of the human TP gene [SEQ ID NO:1,3,5] in a genomic clone has revealed that the DNA sequence encoding amino acid 81 lies in the middle of an exon with no nearby potential splice donor sites, indicating that a TP containing C-terminal sequence similar to the bovine sequence is not produced from the human TP gene [SEQ ID NO:1,3,5].

Protein sequences were searched for motifs in release 9 of the Prosite database [A. Bairoch, *Nucl. Acids Res.*, 21:3097–3103 (1993)] using MacPattern [R. Fuchs, *Comput. Appl. Biosci.*, 7:105–106 (1991)]. This analysis revealed several potential phosphorylation sites for protein kinases, including KTYDAASY, amino acids 619–626 of TPα [620–627 of SEQ ID NO:2], which matches a consensus sequence for phosphorylation by some tyrosine kinases ([K/R]$X_{2/3}$[D/E]$X_{2/3}$Y) [T. Patschinsky et al, *Proc. Natl. Acad. Sci., U.S.A.*, 79:973–977 (1982)].

Hydropathy analysis was performed by the method of D. M. Engelman et al, *Ann. Rev. Biophys. Biophys. Chem.*, 15:321–353 (1986) as implemented in MacVector (Eastman Kodak Chemical Co., software version 4.1) and revealed that TPs β and γ [SEQ ID NOS: 4 and 6] contain a very hydrophobic region close to their carboxy termini that may function as a transmembrane domain. No compelling similarities to previously known protein or nucleic acid sequences other than TP were revealed.

EXAMPLE 3

Expression of Recombinant Human TP in Bacteria

The open reading frames (ORFs) for recombinant human thymopoietin cDNAs α, β, and γ [SEQ ID NOS: 1, 3, 5] have been expressed in *E. coli* using inducible T7 RNA polymerase-dependent pET expression vectors [Novagen; Studier et al, *Meth. Enzymol.*, 185:60–89 (1990)] as follows.

To construct an hTPα expression vector, the ORF was amplified by PCR from λhTP-T.32 and an overlapping Bam HI/Hind III fragment from λhTP-T.153. Primers that introduced an Nhe I site at the 5' end and an Xho I site at the 3' end were used, allowing insertion into the vector pET-17b (Novagen) between the Nhe I and Xho I sites. This construct, called pEThTPe, pETTII, or pET17b-hTPα, encodes hTPα as a fusion protein with three additional amino acids, Met Ala Ser at the amino terminus, followed by the hTPe sequence [SEQ ID NO: 2] beginning with Met Pro Glu.

To construct an hTPβ expression vector, the open reading frame was amplified by PCR from λT.17, using primers that introduced an Nde I site at the 5' end and a BamHI site at the 3' end, allowing ligation into the vector pET-3a. The resulting expression plasmid, called pEThTPβ, pETTIa or pET3ahTPβ, encoded hTPβ [SEQ ID NO: 4] and contained no additional amino acids.

pETHTPγ, pETTIb, or pET3ahTPγ was constructed as described for pEThTPβ, except the open reading frame was amplified from λhTP-T.206.

For expression, the plasmids were transformed into $E.$ $coli$ strain BL21(DE3) [Novagen] which contains the T7 RNA polymerase gene integrated into the chromosome and under the control of the lacUV5 promoter. Induction of transcription from the lacUV5 promoter by addition of isopropyl β-D-thioglucoside [IPTG; Gibco-BRL] produces the T7 RNA polymerase, which in turn transcribes the hTP genes which are under the control of a T7 RNA polymerase-dependent promoter. Cells were grown in M9 medium supplemented with 1% casamino acid [Difco] and 100 µg/mL ampicillin or carbenicillin [Sigma]. When the cell density reached an optical density of 0.3 to 0.5 at 600 nm (at approximately 4 hours), the T7 RNA polymerase was induced by addition of IPTG to 1 mM, and the cells were grown for an additional 4 hours or overnight.

To confirm that the bacteria had been transformed with the appropriate plasmids and that the correct proteins were being produced, lysates of $E.$ $coli$ strains expressing the recombinant TPs were compared to lysates of the human T cell line CEM [American Type Culture Collection, ATCC #CCL 119]. Mammalian cell extracts were prepared by lysing cells in 1% NP-40, 20 mM Tris-HCl pH 7.5, 150 mM NaCl, 1 mM EDTA, 0.1 mM EGTA, 0.5 mM DTT, plus the following protease inhibitors (Boehringer Mannheim):10 µg/ml aprotinin, 0.3 mM pepstatin, 0.1 mM Pefabloc, 1 µg/ml E-64. After passage through a 27 gauge needle 10 times to reduce viscosity and centrifugation to remove insoluble material, sample buffer [U. Laemmli, $Nature$, 227:658–680 (1970)] was added. $E.$ $coli$ extracts were prepared by direct lysis in sample buffer. Proteins were separated by SDS-PAGE in 10% gels (Novex) buffered with tricine, under reducing conditions. Proteins were transferred to nitrocellulose (Novex), and TPs were detected after incubation with an affinity-purified rabbit antiserum raised against a synthetic peptide consisting of amino acids 1 to 19 of the common amino terminal region of TPs α, β and γ [2–20 of SEQ ID NO: 2, 4, 6] and peroxidase-linked goat anti-rabbit Ig (Pierce) using an enhanced chemiluminescence system (Amersham).

The molecular masses of the TPs α, β and γ [SEQ ID NOS: 2, 4, 6] were determined by comparison to marker proteins in separate experiments. Recombinant hTPs α, β, and γ [SEQ ID NOS: 2, 4, 6] produce 75 kDa, 51 kDa and 39 kDa proteins that co-migrated with the major thymopoietin proteins expressed in the human T cell line CEM. See Example 4.

EXAMPLE 4

Characterization of TP Proteins

A. Western Blot Analysis

Recombinant TP α, γ, and γ [SEQ ID NOS: 2, 4, 6] expressed in $E.$ $coli$ were compared with the TP proteins expressed in the human T cell line CEM by immunoblotting as described above.

CEM cells express three major intracellular proteins detected with an antiserum against TP amino acids 1–19, with apparent molecular masses of 75, 51, and 39 kDa. The 75 kDa, 51 kDa, and 39 kDa CEM proteins are the sizes predicted from the cDNA sequences for TPs α, β, and γ, respectively, and co-migrate with recombinant TPs α, β, and γ.

B. Northern Blot Analysis

Poly(A)$^+$ RNA from the human T cell line CEM (ATCC) was prepared by extraction with acid guanidinium thiocyanate-phenol-chloroform [P. Chomczynski et al, $Anal.$ $Biochem.$, 162:156–159 (1987)] using RNAzol (Cinna/Biotecx), followed by selection on oligo-dT columns as described [Sambrook et al, Molecular Cloning: A Laboratory Manual, 2nd Edit., Cold Spring Harbor Laboratories, Cold Spring Harbor, N.Y. (1989).

C. TP mRNAs in T Cell Lines

Probes for detection of TP mRNAs were partially overlapping oligonucleotides that were radiolabelled by extension of 3' ends to generate the complete double stranded sequence. Oligonucleotide sequences used were the sense and antisense (complementary) sequences as follows, α/β/γ sense: nucleotides 1 to 87 [208 to 294 of SEQ ID NO: 1,3,5], antisense: 156 to 64 [363 to 271 of SEQ ID NO: 1,3,5];

α-specific sense: 1488 to 1587 [1695 to 1795 of SEQ ID NO:1], antisense: 1587 to 1570 [1794 to 1777 of SEQ ID NO: 1];

β-specific sense: 849 to 898 [1089 to 1139 of SEQ ID NO:4], antisense: 929 to 879 [1169 to 1119 of SEQ ID NO: 3];

β/γ-specific sense: 1286 to 1330 [1527 to 1571 of SEQ ID NO:3], antisense: 1365 to 1316 [1605 to 1556 of SEQ ID NO: 3]

Three distinct major human TP mRNAs, estimated to be 4.4 kb, 4.1 kb, and 4.0 kb, were detected in CEM cells. All three mRNAs were detected when blots were probed with an oligonucleotide containing sequences encoding amino acids 1 to 52 of the human TPs [2–53 of SEQ ID NO: 2, 4, 6], sequences that are present in TPs α, β, and γ. As none of the cDNAs isolated contain complete 3' untranslated regions, the lengths of TP α, β, and γ mRNAs could not be determined simply from the lengths of the cDNAs. Only the ~4.4 kb mRNA was detected with the β-specific probe, only the ~4.0 kb mRNA was detected with the α-specific probe, and the ~4.1 kb mRNA was detected with the β/γ-specific probe but not with s-specific or β-specific probes, suggesting that the 4.4 kb mRNA encodes TPβ, the 4.0 kb mRNA encodes TPα, and the 4.1 kb mRNA encodes TPγ.

D. Expression of TP mRNAs in adult and fetal tissues

Poly(A)+ RNA from human tissues and blots of human tissue mRNAs were purchased from Clontech. Glyoxylated poly(A)+ RNAs were separated on 1% agarose gels and blotted to nylon membranes (Gibco BRL). Hybridization and washing conditions were as described in Sambrook et al, cited above. Sizes of mRNAs were determined by comparison to RNA size markers (Gibco BRL).

TP mRNAs were detected in all tissues examined, with highest expression in adult thymus and in fetal liver. In some tissues, TP mRNAs of slightly different sizes than the thymus mRNAs were resolved when electrophoresis times were extended. Whether such differences result from different 5' or 3' untranslated regions or additional distinct patterns of alternative splicing of coding exons is not yet known. Expression of TPs α, β, and γ SEQ ID NOS: 2, 4, 6] in many tissues, with particularly high expression in thymus, has also been observed in rodents, and initial analysis of rat TP cDNAs suggests a high level of sequence conservation between rat and human TP α, consistent with important functions of TPs in thymus and other tissues.

EXAMPLE 5

Expression of Recombinant Human TP in Mammalian Cells hTPs α, β, and γ [SEQ ID NOS: 2, 4, 6] were expressed in mammalian cells by PCR amplification of the open reading frames and insertion into the mammalian expression vector pCMV6, a derivative of pCMV1 ]S. Andersson et al, *J. Biol. Chem.*, 264:8222–8229 (1989)] between the Kpn I and Sal I sites for TPα and the Kpn I and Not I sites for TPβ and TPγ. The resulting vectors are transfected into human embryonal kidney 293 cells [American Type Culture Collection, Accession #CRL 1573] by conventional techniques using calcium phosphate precipitation. The transfected cells are cultured in DMEM medium at 37° C. until confluent.

The proteins are then isolated from the cell culture by lysis and conventional purification techniques and authenticated by Western blotting and SDS/PAGE.

EXAMPLE 6

Production of Site-Specific Antibodies to the HTP Sequence— Synthesis of (HFP$_{1-19}$)-Lysine Core The antibodies described below were found to be capable of recognizing the specific peptide sequence within a larger synthetic peptide fragment or natural HTP molecule.

An octameric branched lysine lattice was synthesized as described [Posnett et al, *J. Biol. Chem.*, 263:1719–1725 (1988)] and the protected hTP$_{1-19}$ fragment was synthesized by growth from both the α- and ε-amino groups. An Applied Biosystems model 430A peptide synthesizer was used employing standard protocols and software version 1.4. All amino acids were double-coupled and the end-NH$_2$ program was used to remove the terminal Boc-groups. The protected peptide-resin was treated with liquid hydrogen fluoride, in the presence of p-cresol, p-thiocresol, and dimethylsulfide as scavengers, at 0° C. for 1 hour with constant stirring. Excess HF was removed by vacuum and the residue treated with ether to remove scavenger products. The peptide was extracted (3×50 mL) with 50% acetic acid and the solvents evaporated in vacuo, and the product freeze-dried.

The crude peptide was initially purified on an Amberlite IRA-68 ion-exchange column; further purification was accomplished by reversed-phase HPLC on a preparative C$_{18}$ column. The solvents used were: water containing 0.1% trifluoroacetic acid (TFA) (buffer A) and CH$_3$CN—H$_2$O (4:1) containing 0.1% TFA (buffer B). A linear gradient of 15–30% buffer B over 100 minutes was used. The appropriate fractions containing the peptide were pooled, the solvents evaporated in vacuo, and the product freeze-dried. The purified peptide gave satisfactory amino acid analysis. This peptide was used as an immunogen to raise antibodies as described in Example 7.

EXAMPLE 7

Generation and Routine Testing of Antisera Against Specific Protein Sequences

A. Generation of Antiserum

In order to produce reagents for use in immunoassays for both research and clinical diagnostic purposes, animals, usually rabbits, are repeatedly exposed to a compound in order to initiate an immune response that results in the formation of specific antibodies against that substance. By selecting specific regions of the hTP protein, e.g., those peptides disclosed in Table I above, and synthesizing these regions as smaller peptides, antibodies can be generated that specifically recognize the selected peptide and, the larger hTP as well.

To greatly increase the antigenicity of the selected hTP peptide and assure greater exposure of the sequence of interest a polylysine core compound is designed which employs the multiple reactive sites on lysine to create a network of lysine molecules with repeats of the small hTP peptide as the final layer. Thus the odds of antibodies being generated against the specified hTP peptide sequence are greatly enhanced.

Antisera are produced by injecting emulsions comprised of the polylysine core compound and an adjuvant into laboratory animals, preferably rabbits or sheep (mice are preferred for monoclonal preparation), to help stimulate the immune response. The injections are given in multiple sites and at regular time intervals in order to create repeated exposures from several routes. After sufficient exposure to stimulate an immune response, e.g., about 40 days, sera is collected from the rabbits and tested for the presence of antibodies against the injected peptide sequence.

B. Testing of Antiserum Titers

Enzyme-Linked Immunoassay (ELISA): In order to determine the concentration of specific antibodies present in the sera against the peptide of interest, serial dilutions of the test sera are added to wells of a microtiter plate that has been coated with the peptide used to generate the antiserum. After allowing time for the antibodies to bind to the coated peptide, the unbound sera is washed from the plate. A solution containing enzyme-linked antibodies that recognize immunoglobulins of the species in which the antisera was generated (e.g., anti-rabbit IgG antibodies) is added to the wells. These "anti-rabbit" antibodies bind to the rabbit antibodies that are bound to the peptide coated plate; thus, enzyme molecules (horseradish peroxidase) are effectively placed at each site where an antibody initially bound to the peptide coated plate. The unbound "anti-rabbit" antibodies are then washed from the plate. A substrate, which when converted by the enzyme to a different molecular form results in a color reaction, is added to the wells.

The intensity of the color change is quantitated and used to determine the relative concentration of antibodies that bound to the peptide coated peptide. For purposes of comparison, the amount of antibody present (titer) is expressed as the concentration of antiserum required to produce a final color reaction with optical density of 1.0. This intensity generally represents a maximal response. Antisera showing sufficient titer are further characterized to determine both their full specificity and their utility in the various immuno-applications.

C. Results

Rabbits immunized with multiple antigenic peptides corresponding to amino acid sequences derived from the cDNAs of the invention yielded antiserums with the following titers (titer yielding 1.00D unit by ELISA):

| Peptides | Titers | SEQ ID NO |
|---|---|---|
| αβγ 1–19 | $8 \times 10^6$ | (2–20) 2, 4, 6 |
| αβγ 28–39 | $4 \times 10^5$ | (29–40) 2, 4, 6 |
| αβγ 29–50 | $1.2 \times 10^7$ | (30–51) 2, 4, 6 |
| αβγ 40–52 | $1.6 \times 10^7$ | (41–53) 2, 4, 6 |
| αβγ 56–71 | $1.5 \times 10^6$ | (57–72) 2, 4, 6 |
| αβγ 92–108 | $8 \times 10^6$ | (93–109) 2, 4, 6 |
| α 168–187 | $2 \times 10^5$ | (169–188) 2, 4, 6 |
| α 233–253 | $2 \times 10^6$ | (234–254) 2 |
| α 342–362 | $8 \times 10^6$ | (343–363) 2 |
| α 425–443 | $2.5 \times 10^5$ | (426–444) 2 |
| α 518–538 | $3 \times 10^6$ | (519–539) 2 |
| α 604–622 | $1.5 \times 10^6$ | (605–623) 2 |
| α 188–197 | $2.5 \times 10^5$ | (189–198) 2 |
| βγ1 196–215 | $1 \times 10^6$ | (197–216) 4, 6 |
| β 247–265 | $6 \times 10^6$ | (248–266) 4 |
| β 312–329 | $3 \times 10^6$ | (313–330) 4 |
| βγ2 332–348 | $3 \times 10^6$ | (333–349) 4 (224–240) 6 |
| βγ2 397–412 | $3 \times 10^6$ | (398–413) 4 (289–304) 6 |

EXAMPLE 8

Preparation of Monoclonal Antibodies Specific for Thymopoietin

A. Immunization

Synthetic peptide sequences (derived from the predicted protein sequences of each of three thymopoietin cDNAs) of approximately 20 amino acid residues were built on a branched core of seven lysine residues according to the method of Tam [see, e.g., Posnett et al, cited above]. These structures are referred to as multiple antigenic peptides (MAP). In particular, mice were immunized with the HTPαβγ sequence specified by residues 29–50 (GEQRKDVYVQLYLQHLTARNRP)$_8$K$_7$G [30–51 of SEQ ID NO: 2, 4, 6].

Balb/c mice, 8–12 weeks of age, were injected with 50 μg of MAP suspended in 200 μl of adjuvant which was divided between the subcutaneous and peritoneal routes. The adjuvant for the first injection was either Ribi™ (Ribi ImmunoChem, Hamilton, Mont.) or complete Freund's adjuvant. For subsequent injections, Ribi™ or incomplete Freund's adjuvant was used. A minimum of four injections (but more often 6–10) were given at no less than two week intervals. Sera were collected from animals 5 days following a booster injection in order to monitor antibody response. The reactivity of test sera with the specific MAP immunogen was measured by ELISA. Sera with high titers to the specific MAP were tested by western blot for binding to the native TP present in lysates of the T cell line CEM [ATCC; CCL 119]. Only mice which had serum showing high titers to the specific MAP and detectable binding to native TP were considered for fusion.

B. Fusion

Splenocytes from immunoresponsive mice, in particular, a mouse immunized with HTP$_{29-50}$ MAP, were mixed with P3X63Ag8U1 (HGPRT myeloma) cells [obtained from Dr. Matthew D. Scharff, Einstein University, Bronx, N.Y.] at a ratio of 1:1. Cell fusion was accomplished by treating the pelleted cells with 40% polyethylene glycol 4000 essentially as described in G. Kohler and C. Milstein, *Nature*, 256:495 (1975). Hybridomas were grown in HAT selection medium as 1000 independent cultures and supernatants from the cultures were screened for TP-specific MAb production about 2 weeks after fusion.

C. Hybridoma Selection

Selection for hybridomas producing TP-specific monoclonal antibodies was achieved by testing culture supernatants in ELISA systems in which the antigen on the plate was either bovine serum albumin (BSA) or the immunizing peptide. Supernatants negative for BSA and positive for the immunizing peptide were tested on additional synthetic peptides or enriched preparations of native TP and the hybridomas producing supernatants positive for only HTP$_{29-50}$ containing synthetic peptides and the TP-enriched native materials were chosen for subcloning. Hybridoma clones arising from a single cell were isolated by two successive rounds of limit dilution plating. For the HTPαβγ$_{29-50}$ lysine core immunogen, three independent hybridomas (885–1.7B8, 885–1.6E10 & 885–1.1C6) were identified and cloned.

D. MAb Characterization

Anti-TP monoclonal antibodies, purified from murine ascites fluid, were shown to be specific for native Tp by the immunostaining profile observed on western blots of cell lysates prepared from the early T cell line CEM. Three proteins of apparent molecular sizes of 75 kDa, 51 kDa and 39 kDa (the sizes predicted by the TP cDNA sequences and verified by expression of the TP cDNA's in *E. coli*) were detected by the anti-HTP$_{29-50}$ monoclonal antibodies. Preincubation of the antibodies with the synthetic HTP$_{29-50}$ peptide but not with an irrelevant synthetic peptide resulted in the loss of immunostaining of the protein bands. This suggests that the protein bands recognized by the monoclonal antibodies are TP proteins.

E. Other TP-Specific MAbs

Other monoclonal antibodies specific for one or more of the TP proteins, were obtained by immunization with MAP immunogens. These include those reported in Table II below.

TABLE II

| MAP | MAb | TP Proteins |
|---|---|---|
| HTPαβγ 1–19 | 850-1.10A8 | αβγ |

TABLE II-continued

| MAP | MAb | TP Proteins |
|---|---|---|
| | 850-1.10F8 | αβγ |
| HTPβ 312–329 | 937-1.6G11 | β |
| | 937-1.2B11 | β |
| HTPα 233–253 | 923-2.9F5 | α |

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A polynucleotide sequence encoding a thymopoietin protein, said sequence isolated from the cellular material with which it is naturally associated, which is selected from the group consisting of
   (a) SEQ ID NO: 1,
   (b) SEQ ID NO: 3,
   (c) SEQ ID NO: 5, and
   (d) a sequence complementary to any of sequences (a) through (c).

2. A vector comprising a polynucleotide sequence according to claim 1.

3. A host cell transformed by a vector according to claim 2.

4. The host cell according to claim 3 wherein said polynucleotide is operably linked to a heterologous expression control sequence capable of directing the expression of the protein encoded by said sequence in a selected host cell.

5. The host cell according to claim 3 selected from the group consisting of bacterial, fungal, insect, and mammalian cells.

6. The host cell according to claim 5 wherein said cell is *E. coli.*

7. A method for producing recombinant human thymopoietin comprising incubating a transformed host cell comprising the polynucleotide sequence of claim 1 encoding human thymopoietin under conditions that allow expression of the human thymopoietin and recovering the thymopoietin therefrom.

8. A method of producing recombinant human thymopoietin comprising:

(a) providing a host cell and an expression vector comprising the polynucleotide sequence of claim 1 encoding human thymopoietin operably linked to an expression control sequence directing the expression of the human thymopoietin;

(b) incubating the host cell under conditions which allow transfection of the host cell by the vector and expression of the human thymopoietin; and (c) recovering said recombinant human thymopoietin.

9. The method according to claim 8 wherein said conditions permit the secretion of the human thymopoietin.

10. A diagnostic reagent comprising a polynucleotide sequence of claim 1 and a detectable label.

11. A polynucleotide sequence encoding a thymopoietin protein, said sequence isolated from the cellular material with which it is naturally associated, which is selected from the group consisting of SEQ ID NO: 1 and a sequence complementary thereto.

12. A polynucleotide sequence encoding a thymopoietin protein, said sequence isolated from the cellular material with which it is naturally associated, which is selected from the group consisting of SEQ ID NO: 3 and a sequence complementary thereto.

13. A polynucleotide sequence encoding a thymopoietin protein, said sequence isolated from the cellular material with which it is naturally associated, which is selected from the group consisting of SEQ ID NO: 5 and a sequence complementary thereto.

* * * * *

UNITED STATES PATENT AND TRADEMARK OFFICE
CERTIFICATE OF CORRECTION

PATENT NO. : 5,472,856
DATED : December 5, 1995
INVENTOR(S) : Crafford A. Harris, Gideon Goldstein, John J. Siekierka, Mary A. Talle, Ponniah Shenbagamurthi, Michael D. Culler, and Diane R. Setcavage It is certified that error appears in the above-indentified patent and that said Letters Patent is hereby corrected as shown below:

Col. 5, line 18, delete "TPB" and insert thereof -- TPβ --.

Col. 11, line 7, delete "pEThTPe" and insert thereof -- pEThTPα --.

Col. 11, line 9, delete "hTPe" and insert thereof -- hTPα --.

Col. 12, line 65, delete "s-specific" and insert thereof -- α-specific --.

Col. 13, line 48, in the title under Example 6, delete "(HFP$_{1-19}$)-Lysine" and insert thereof -- (HTP$_{1-19}$)$_8$-Lysine --.

Col. 15, line 9, before the word "maximal", insert -- 50% --.

Col. 15, line 19, delete "1.00D" and insert thereof -- 1.0 OD --.

Col. 15, line 28, in the first column in the table under the heading "Peptides", delete "α 168-187" and insert thereof -- αβγ 168-187 --.

Signed and Sealed this

Twenty-third Day of April, 1996

Attest:

BRUCE LEHMAN

Attesting Officer

Commissioner of Patents and Trademarks